United States Patent
Battaglini et al.

(10) Patent No.: US 11,587,665 B2
(45) Date of Patent: Feb. 21, 2023

(54) METHODS, SYSTEMS, AND NON-TRANSITORY COMPUTER READABLE MEDIA FOR ESTIMATING MAXIMUM HEART RATE AND MAXIMAL OXYGEN UPTAKE FROM SUBMAXIMAL EXERCISE INTENSITIES

(71) Applicants: The University of North Carolina at Chapel Hill, Chapel Hill, NC (US); Duke University, Durham, NC (US)

(72) Inventors: Claudio Luiz Battaglini, Durham, NC (US); Brian Patrick Mann, Durham, NC (US); Michael Joseph Mazzoleni, Morrisville, NC (US)

(73) Assignees: THE UNIVERSITY OF NORTH CAROLINA AT CHAPEL HILL, Chapel Hill, NC (US); DUKE UNIVERSITY, Durham, NC (US)

( * ) Notice: Subject to any disclaimer, the term of this patent is extended or adjusted under 35 U.S.C. 154(b) by 1274 days.

(21) Appl. No.: 16/066,920

(22) PCT Filed: Dec. 28, 2016

(86) PCT No.: PCT/US2016/068814
§ 371 (c)(1),
(2) Date: Jun. 28, 2018

(87) PCT Pub. No.: WO2017/117183
PCT Pub. Date: Jul. 6, 2017

(65) Prior Publication Data
US 2019/0009134 A1    Jan. 10, 2019

Related U.S. Application Data

(60) Provisional application No. 62/271,411, filed on Dec. 28, 2015.

(51) Int. Cl.
*G16H 20/30* (2018.01)
*A61B 5/11* (2006.01)
(Continued)

(52) U.S. Cl.
CPC ............. *G16H 20/30* (2018.01); *A61B 5/024* (2013.01); *A61B 5/0205* (2013.01); *A61B 5/091* (2013.01);
(Continued)

(58) Field of Classification Search
CPC ........ G16H 20/30; G16H 50/20; G16H 50/50; G16H 40/63; G09B 19/0038;
(Continued)

(56) References Cited

U.S. PATENT DOCUMENTS

| 8,094,907 B1 | 1/2012 | Meyer et al. |
| 2011/0288381 A1* | 11/2011 | Bartholomew ........ A61B 5/024 600/300 |

(Continued)

FOREIGN PATENT DOCUMENTS

| KR | 10-2011-0034863 | 4/2011 | |
| KR | 20110034863 A * | 4/2011 | ............. A61B 5/224 |

OTHER PUBLICATIONS

Google Patents, English Translation of KR20110034863A.*
(Continued)

*Primary Examiner* — Jay Trent Liddle
*Assistant Examiner* — Alyssa N Brandley
(74) *Attorney, Agent, or Firm* — Jenkins, Wilson, Taylor & Hunt, P.A.

(57) ABSTRACT

A system for estimating maximum heart rate and maximal oxygen uptake from submaximal exercise intensities can include an exercise intensity monitor, a cardiopulmonary monitor, and one or more computers. The computers can be configured, by virtue of appropriate programming, to receive
(Continued)

submaximal exercise intensity data from the exercise intensity monitor and submaximal cardiopulmonary data from the cardiopulmonary monitor while a user, who coupled to the exercise intensity monitor and the cardiopulmonary monitor, is performing an exercise at a submaximal exercise intensity. The one or more computers then determine a heuristic estimate of a maximal cardiopulmonary state of the user based on the submaximal exercise intensity data and the submaximal cardiopulmonary data.

31 Claims, 12 Drawing Sheets

(51) Int. Cl.
| | |
|---|---|
| A61B 5/024 | (2006.01) |
| A61B 5/00 | (2006.01) |
| A61B 5/0205 | (2006.01) |
| A61B 5/091 | (2006.01) |
| G16H 50/20 | (2018.01) |
| G16H 40/63 | (2018.01) |
| G09B 19/00 | (2006.01) |
| G16H 50/50 | (2018.01) |

(52) U.S. Cl.
CPC .......... *A61B 5/1118* (2013.01); *A61B 5/7267* (2013.01); *G09B 19/0038* (2013.01); *G16H 40/63* (2018.01); *G16H 50/20* (2018.01); *G16H 50/50* (2018.01); *A61B 2503/10* (2013.01)

(58) Field of Classification Search
CPC ... A61B 2503/10; A61B 5/0205; A61B 5/024; A61B 5/091; A61B 5/1118; A61B 5/7267; A61B 5/00
See application file for complete search history.

(56) References Cited

U.S. PATENT DOCUMENTS

| | | | | |
|---|---|---|---|---|
| 2014/0323820 | A1* | 10/2014 | Schwiening | A61B 5/0205 600/301 |
| 2015/0088006 | A1* | 3/2015 | Rapoport | A61B 5/1112 600/484 |
| 2015/0209585 | A1* | 7/2015 | Lineaweaver | A61N 1/36039 607/57 |

OTHER PUBLICATIONS

Notification of Transmittal of the International Search Report and the Written Opinion of the International Searching Authority, or the Declaration for International Application No. PCT/US2016/068814 (dated Apr. 13, 2017).
Zakynthinaki et al., "Modelling Heart Rate Kinetics," PLoS One, vol. 10, No. 4, p. 1-26 (Apr. 13, 2015).
Rao, "Engineering Optimization: Theory and Practice," Fourth Edition, John Wiley & Sons, Inc., pp. 1-830 (2009).
DiMenna et al., "Linear" Versus "Nonlinear" VO2 Responses to Exercise: Reshaping Traditional Beliefs, Journal of Exercise Science and FItness, vol. 7, No. 2, pp. 67-84 (2009).
Zakynthinaki et al., "Stochastic optimization for the calculation of the time dependency of the physiological demand during exercise and recovery," Computer Physics Communications, vol. 179, No. 12, pp. 888-894 (2008).
Stirling et al., "Modeling and Analysis of the Effect of Training on V $O_2$ Kinetics and Anaerobic Capacity," Bulletin of Mathematical Biology, vol. 70, No. 5, pp. 1348-1370 (2008).
Stirling et al., "A model of heart rate kinetics in response to exercise," Journal of Nonlinear Mathematical Physics, vol. 15, No. 3, pp. 426-436 (2008).
Zakynthinaki et al, "Stochastic optimization for modeling physiological time series: application to the heart rate response to exercise," Computer Physics Communications, vol. 176, No. 2, pp. 98-108 (2007).
Stirling et al., "A model of oxygen uptake kinetics in response to exercise: Including a means of calculating oxygen demand/decit/debt," Bulletin of Mathematical Biology, vol. 67, No. 5, pp. 989-1015 (2005).
Robergs et al., "The surprising history of the HRmax=220-age equation," Journal of Exercise Physiology Online, vol. 5, No. 2, pp. 1-10 (2002).
Miller et al., "Genetic Algorithms, Selection Schemes, and the Varying Effects of Noise," Evolutionary Computation, vol. 4, No. 2, pp. 113-131 (1996).
Goldberg, "Genetic Algorithms in Search, Optimization and Machine Learning," Addison-Wesley Publishing Company, Inc., pp. 1-432 (1989).
Mazzoleni et al., "Modeling and predicting heart rate dynamics across a broad range of transient exercise intensities during cycling," Sports Eng, vol. 19, pp. 1-12 (2016).
"ASME 2015 Program," IDETC/CIE 2015 International Design Engineering Technical Conferences & Computers and Information in Engineering Conference, pp. 1-252 (2015).
Garcia-Ramos et al., "Training load quantification in elite swimmers using a modified version of the training impulse method," European Journal of Sport Science, vol. 15, No. 2, pp. 85-93 (2015).
Battaglini et al., "Twenty-five years of research on the effects of exercise training in breast cancer survivors: A systematic review of the literature," World J Clin Oncol, vol. 5, No. 2, pp. 177-190 (May 10, 2014).
Flouris et al., "Changes in heart rate variability during the induction and decay of heat acclimation," Eur J Appl Physiol, vol. 114, pp. 2119-2128 (2014).
Haddad et al., "Modelling and regulating of cardio-respiratory response for the enhancement of interval training," BioMedical Engineering OnLine, vol. 13, No. 9, pp. 1-14 (2014).
Lefever et al., "Time-variant modelling of heart rate responses to exercise intensity during road cycling," European Journal of Sport Science, vol. 14, No. S1, pp. S406-S412 (2014).
Clarke et al., "Rationale and resources for teaching the mathematical modeling of athletic training and performance," Adv Physiol Educ, vol. 37, pp. 134-152 (2013).
De Winter, "Using the Student's t-test with extremely small sample sizes," Practical Assessment, Research & Evaluation, vol. 18, No. 10, pp. 1-12 (Aug. 2013).
Wood et al., "Cardiopulmonary fitness in patients undergoing hematopoietic SCT: a pilot study," Bone Marrow Transplantation, vol. 48, pp. 1342-1349 (2013).
Mann et al., "Using information to generate derivative coordinates from noisy time series," Commun Nonlinear Sci Numer Simulat, vol. 16, pp. 1-6 (2011).
Su et al., "Dynamic Modelling of Heart Rate Response Under Different Exercise Intensity," The Open Medical Informatics Journal, vol. 4, pp. 81-85 (2010).
Stupnicki et al., "Fitting a Single-Phase Model to the Post-Exercise Changes in Heart Rate and Oxygen Uptake," Physiological Research, vol. 59, pp. 1-7 (2010).
"The Engineering of Sport 7," Springer, vol. 1, pp. 1-695 (2008).
Johnson, "Biomechanics and Exercise Physiology," Quantitative Modeling, CRS Press, pp. 1-686 (2007).
Su et al., "Identification and Control for Heart Rate Regulation During Treadmill Exercise," IEEE Transactions on Biomedical Engineering, vol. 54, No. 7, pp. 1238-1246 (Jul. 2007).
Mavrommataki et al., "Recovery of Power Output and Heart Rate Kinetics During Repeated Bouts of Rowing Exercise with Different Rest Intervals," Journal of Sports Science and Medicine, vol. 5, pp. 115-122 (2006).
Acharya et al., "Classification of cardiac abnormalities using heart rate signals," Medical & Biological Engineering & Computing, vol. 42, pp. 1-6 (2004).

(56) References Cited

OTHER PUBLICATIONS

Uth et al., "Estimation of VO2 max from the ratio between HRmax and HRrest—the Heart Rate Ratio Method," Eur J Appl Physiol, vol. 91, pp. 111-115 (2004).

Achten et al., "Heart Rate Monitoring," Review Article, Sports Med, vol. 33, No. 7, pp. 517-538 (2003).

Coggan, "Training and racing using a power meter: an introduction," VeloPres, pp. 1-22 (Mar. 25, 2003).

Taha et al., "Systems Modelling of the Relationship Between Training and Performance," Sports Med, vol. 33, No. 14, pp. 1-13 (2003).

Bearden et al., "VO2 and heart rate kinetics in cycling: transitions from an elevated baseline," J Appl Physiol, vol. 90, pp. 2081-2087 (2001).

Tanaka et al., "Age-Predicted Maximal Heart Rate Revisited," Journal of the American College of Cardiology, vol. 37, No. 1, pp. 153-156 (2001).

Strogatz, "Nonlinear Dynamics and Chaos," Perseus Books, pp. 1-505 (1994).

Abarbanel, "The analysis of observed chaotic data in physical systems," Reviews of Modern Physics, vol. 65, No. 4, pp. 1332-1392 (Oct. 1993).

Cohen, "Statistical Power Analysis for the Behavioral Sciences, Second Edition," Lawrence Erlbaum Associates, Publishers, pp. 1-579 (1988).

Kline et al., "Estimation of VO2max from a one-mile track walk, gender, age, and body weight," Medicine and Science in Sports and Exercise, vol. 19, No. 3, pp. 253-259 (1987).

Londeree et al., "Effect of Age and Other Factors on Maximal Heart Rate," Research Quarterly for Exercise and Sport, vol. 53, No. 4, pp. 1-9 (1982).

Calvert et al., "A Systems Model of the Effects of Training on Physical Performance," IEEE Transactions on Systems, Man, and Cybernetics, vol. SMC-6, No. 2, pp. 94-102 (Feb. 1976).

Givoni et al., "Predicting effects of heat acclimatization on heart rate and rectal temperature," Journal of Applied Physiology, vol. 35, No. 6, pp. 1-5 (Dec. 1973).

Givoni et al., "Predicting heart rate response to work, environment, and clothing," Journal of Applied Physiology, vol. 34, No. 2, pp. 1-4 (Feb. 1973).

\* cited by examiner

METHODS, SYSTEMS, AND NON-TRANSITORY COMPUTER READABLE MEDIA FOR ESTIMATING MAXIMUM HEART RATE AND MAXIMAL OXYGEN UPTAKE FROM SUBMAXIMAL EXERCISE INTENSITIES

PRIORITY CLAIM

This application claims the benefit of U.S. Provisional Application Ser. No. 62/271,411, filed Dec. 28, 2015, the disclosure of which is incorporated herein by reference in its entirety.

TECHNICAL FIELD

This specification relates generally to modeling and predicting heart rate and oxygen uptake dynamics, e.g., to estimate maximum heart rate and maximal oxygen uptake from submaximal exercise intensities.

BACKGROUND

Maximal oxygen uptake ($\dot{V}O_{2max}$) has traditionally been viewed as the best single measurement of overall health and fitness in humans. The most accurate method for determining maximal oxygen uptake is a maximal cardiopulmonary exercise test (CPET) using indirect calorimetry, during which an individual exercises at increasing intensity levels until volitional fatigue is reached. However, a maximal cardiopulmonary exercise test is not always practical or feasible, as it poses an unnecessary and unacceptable health risk for certain populations. The test also requires expensive equipment and specialized personnel which are not always readily available at medical clinics, hospitals, and training centers. Additionally, the accurate determination of maximal oxygen uptake from a maximal cardiopulmonary exercise test is no trivial task, and a proper assessment requires the careful analysis of multiple physiological factors. In the absence of a maximal cardiopulmonary exercise test, maximal oxygen uptake is typically estimated using submaximal exercise protocols and population-specific regression equations. However, these estimation methods have well-known limitations due to simplifying assumptions made during the model development process, and their predictions for maximal oxygen uptake are typically associated with a large degree of uncertainty and error. Many submaximal estimation methods are based on the concept of linear extrapolation, which assumes a linear relationship between heart rate (HR), oxygen uptake ($\dot{V}O_2$), and exercise intensity. Many submaximal estimation methods also assume uniform mechanical efficiency throughout the protocol, despite the fact that mechanical efficiency is related to oxygen consumption, which is heavily influenced by the fitness level of an individual and their personal genetics. However, perhaps the greatest source of error in submaximal maximal oxygen uptake estimation methods is their reliance on maximum heart rate ($HR_{max}$) as predicted by age-based regression equations.

The heart rate response of an individual is intrinsically related to their oxygen uptake response. In the absence of a maximal oxygen uptake assessment, maximum heart rate is often used to prescribe exercise intensities for training and rehabilitation. As is the case for maximal oxygen uptake, the most accurate method for determining maximum heart rate is a maximal cardiopulmonary exercise test. However, in practice, maximum heart rate is often determined using the ubiquitous "$HR_{max}=220-\text{age}$" equation or some other alternative age-based regression equation. While the overall population trend of maximum heart rate declining with age is indisputable, it is still subject to large amounts of inter-individual variability. Therefore, age-based regression equations for maximum heart rate typically have a large standard error of the estimate (SEE) exceeding 10 beats per minute (bpm), which can make it difficult to prescribe accurate heart rate-based training using the age-predicted maximum heart rate. These large estimation errors can cause further problems when they are introduced into a maximal oxygen uptake estimation process via linear extrapolation or a regression analysis, as the errors can propagate throughout the system and become magnified. Therefore, there is a pressing need for the development of submaximal methods for assessing maximum heart rate and maximal oxygen uptake that can approach the accuracy and precision of a maximal cardiopulmonary exercise test.

SUMMARY

A system for estimating maximum heart rate and maximal oxygen uptake from submaximal exercise intensities can include an exercise intensity monitor, a cardiopulmonary monitor, and one or more computers. The computers can be configured, by virtue of appropriate programming, to receive submaximal exercise intensity data from the exercise intensity monitor and submaximal cardiopulmonary data from the cardiopulmonary monitor while a user, who coupled to the exercise intensity monitor and the cardiopulmonary monitor, is performing an exercise at a submaximal exercise intensity. The one or more computers then determine a heuristic estimate of a maximal cardiopulmonary state of the user based on the submaximal exercise intensity data and the submaximal cardiopulmonary data.

The subject matter described in this specification may be implemented in hardware, software, firmware, or combinations of hardware, software and/or firmware. In some examples, the subject matter described in this specification may be implemented using a non-transitory computer-readable medium storing computer executable instructions that when executed by one or more processors of a computer cause the computer to perform operations.

Computer-readable media suitable for implementing the subject matter described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer-readable medium that implements the subject matter described in this specification may be located on a single device or computing platform or may be distributed across multiple devices or computing platforms.

DESCRIPTION

Figure 1:
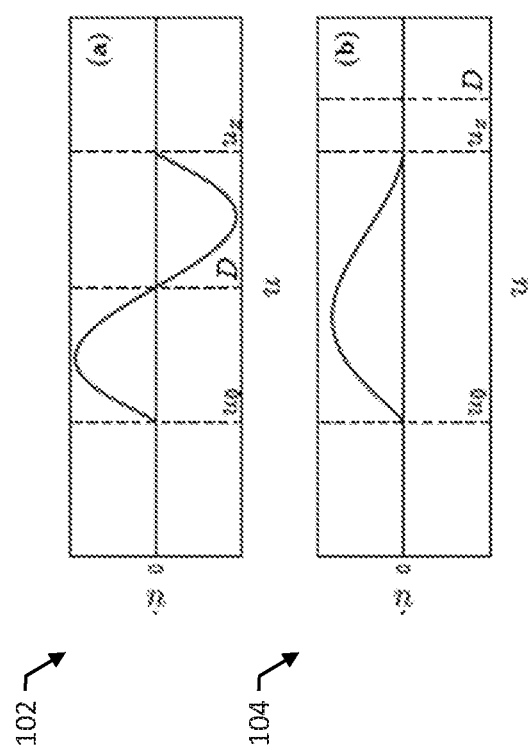
FIG. 1 shows two charts illustrating a 1-D phase plane analysis of heart rate and oxygen uptake dynamics.

A computer system can use an equilibria-based mathematical model and a heuristic parameter estimation algorithm to accurately estimate the maximum heart rate and maximal oxygen uptake of individuals using physiological data collected at submaximal exercise intensities, and the estimation method offers a superior alternative in terms of accuracy and practicality to other current submaximal methods. There are many different populations ranging from normally exercising individuals to amateur and professional athletes to clinical patients that are interested in determining their maximum heart rate and maximal oxygen uptake, as these are valuable parameters for assessing the overall health and fitness of an individual and can be used to make intelligent training decisions for athletes and to determine appropriate treatment options for patients. The computer system can be integrated with existing physiological data collection technologies, and the recent growth in usage and popularity of portable fitness tracker technologies would enable the computer system to be accessible to a large and diverse population of individuals.

Current methods for estimating maximum heart rate and maximal oxygen uptake from submaximal exercise intensities are often inaccurate for a variety of reasons. Most of these methods fail to account for inter-individual physiological variations and instead rely on statistical correlations for specific populations. These methods also often assume that heart rate and oxygen uptake respond linearly to exercise intensity, which is not representative of the actual physiological dynamics. The systems and methods described in this specification include a nonlinear person-specific model of heart rate and oxygen uptake dynamics and a heuristic parameter estimation algorithm for predicting maximum heart rate and maximal oxygen uptake from submaximal exercise intensities.

Human subject tests have validated the method for predicting maximum heart rate and maximal oxygen uptake from submaximal exercise intensities. The participants in the human subject tests each performed a maximal cardiopulmonary exercise test (CPET) in the laboratory to determine their maximum heart rate and maximal oxygen uptake. Some subjects performed the test on an electronically-braked cycle ergometer, and other subjects performed the test on a treadmill. The subjects then returned to the laboratory within a week of the initial test to perform a submaximal cardiopulmonary exercise test on the same equipment that they were initially tested on. A computer system then applied the model and parameter estimation algorithm to their submaximal exercise data to make predictions for their maximum heart rate and maximal oxygen uptake. The submaximal model predictions were compared to the true experimental values obtained during the maximal cardiopulmonary exercise test and reported a coefficient of determination ($R^2$) of 0.96 and a standard error of the estimate (SEE) of 2.4 bpm for maximum heart rate and a coefficient of determination of 0.93 and a standard error of the estimate of 2.1 mL·kg$^{-1}$·min$^{-1}$ for maximal oxygen uptake. For comparison, traditional submaximal estimation methods report a standard error of the estimate of at least 10 bpm for maximum heart rate and a standard error of the estimate of at least 4 mL·kg$^{-1}$·min$^{-1}$ for maximal oxygen uptake.

Mathematical Model

A state equation for heart rate dynamics and oxygen uptake dynamics can be derived from the equilibria and stability of the physiological systems. The model for heart rate dynamics has the same functional form as the model for oxygen uptake dynamics, so for simplicity's sake both heart rate and oxygen uptake will be represented by u during the model derivation. In operation, the two models are handled separately for making predictions.

There are three possible equilibria ũ for the heart rate and oxygen uptake of an individual: the resting value $ũ=u_0$, the maximum value $ũ=u_x$, and the demand value $ũ=D$, which is related to exercise intensity. These equilibria can be used to construct a model of heart rate and oxygen uptake dynamics using the following first order nonlinear ordinary differential equation, $$\dot{u}=A(u-u_0)^\alpha(u_x-u)^\beta(D-u)^\gamma, \tag{1}$$

where A, α, β, and γ are constants related to an individual's personal physiology and fitness and $\dot{u}=du/dt$ (time derivative of u). The parameter A determines the rate at which heart rate and oxygen uptake seek to stabilize at their steady-state value, while α, β, and γ are related to the sensitivity to the respective equilibria ($u_0$, $u_x$, and D). The heart rate and oxygen uptake of an individual can never drop below the resting value or exceed the maximum value, so $u_0 \leq u \leq u_x$. The demand value D will always be greater than the resting value, but it is not necessarily less than the maximum value. A bifurcation occurs at $D=u_x$, which results in two distinct regions of dynamic behavior, as illustrated in FIG. 1.

FIG. 1 shows two charts illustrating a 1-D phase plane analysis of heart rate and oxygen uptake dynamics. A bifurcation occurs at $D=u_x$, resulting in two distinct regions of dynamic behavior for (a) $u_0 \leq D \leq u_x$ (as illustrated in a top chart 102) and (b) $D>u_x$ (as illustrated in a bottom chart 104). The equilibrium at $ũ=D$ is always stable for $u_0 \leq D \leq u_x$, as an individual's heart rate and oxygen uptake will always seek to stabilize at the value demanded by the body in response to exercise. When $D<u_x$, an individual's heart rate and oxygen uptake will attempt to satisfy the demand but cannot exceed the $u_x$ threshold.

Accounting for demand is useful for accurately modeling the heart rate and oxygen uptake response of an individual across a broad range of transient exercise intensities. An individual's heart rate and oxygen uptake will seek to stabilize at the value demanded by the body. This demand value is determined by exercise intensity, and the following first order differential equation can be used to model the dynamics of heart rate and oxygen uptake demand, $$\dot{D}=B(f(\vec{\psi})-D)^\kappa, \tag{2}$$

where B and κ are constants related to an individual's personal physiology and fitness, $f(\vec{\psi})$ is the exercise intensity function (sometimes referred to as the drive function), $\vec{\psi}$ is the exercise intensity input vector, and $\dot{D}=dD/dt$ (time derivative of D). The parameters B and κ govern the rate at which the demand seeks to stabilize at its steady-state value as determined by the exercise intensity function. The nature of the exercise intensity function $f(\vec{\psi})$ and the exercise intensity input vector $\vec{\psi}$ are related to the active mode of exercise. These modes of exercise may include, but are not limited to, walking, jogging, running, cycling, or swimming. The exercise intensity function $f(\vec{\psi})$ may take many forms, and it is often based on a priori knowledge concerning the active mode of exercise. Alternatively, a generic form for the exercise intensity function $f(\vec{\psi})$ may be used. The exercise intensity input vector $\vec{\psi}$ is composed of input variables related to the active mode of exercise, so $\vec{\psi} = \langle \psi_1, \psi_2, \psi_3, \ldots, \psi_{n-1}, \psi_n \rangle$ where each of the individual $\psi$ terms represents an individual exercise intensity input variable and n variables are considered. The exercise intensity input vector is a function of time, so it may be expressed as $\vec{\psi} = \vec{\psi}(t) = \langle \psi(t), \psi_2(t), \psi_3(t), \ldots, \psi_{n-1}(t), \psi_n(t) \rangle$, where (t) indicates a dependence on time. However, for simplicity's sake, the time dependence will be implied in further notation.

Figure 2:
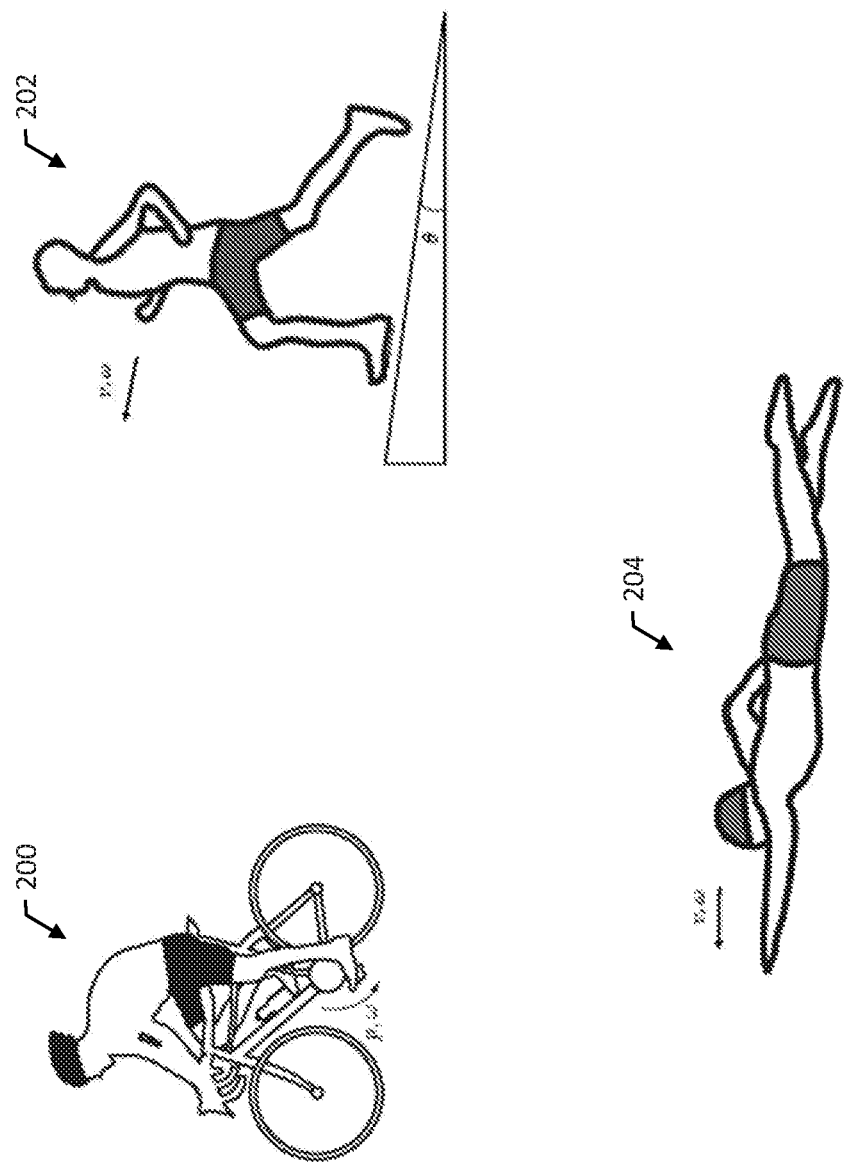
FIG. 2 is a schematic diagram highlighting several possible exercise intensity inputs for the exercise modes of cycling, running, and swimming.

For the case of cycling, the exercise intensity input vector may be expressed as $\vec{\psi} = \langle p, \omega \rangle$, where p is the power output of an individual and CD is their cadence, or frequency of an individual's foot turnover during cycling. FIG. 2 contains a schematic diagram of a cyclist 200 showing how power output p and cadence $\omega$ are related to foot turnover during pedaling. It should be noted that $p = \tau\omega$, where $\tau$ is the torque applied by the cyclist while pedaling. FIG. 2 also illustrates a runner 202 and a swimmer 204. Measuring exercise intensity for running and swimming is discussed further below.

Many current methods for predicting heart rate and oxygen uptake responses during cycling relate power output directly to exercise intensity. However, power output alone may not be sufficient to correctly describe exercise intensity. For example, the same power output can be generated by the application of a large torque at a low cadence or a low torque at a high cadence. These two cases require different muscle recruitment patterns and oxygen demands, even though the power output is the same. By defining exercise intensity as a multi-variable function of power output and cadence, the model is now able to more accurately represent the physiological processes that are active during cycling. In the event that cadence data is not available for whatever reason, the exercise intensity input vector may be expressed as $\vec{\psi} = \langle p \rangle$. However, this definition of exercise intensity may reduce the accuracy of model predictions. This loss of accuracy is somewhat mitigated if the individual is exercising at a relatively constant cadence though.

The exercise intensity input vector for cycling is not limited to be defined as $\vec{\psi} = \langle p, \omega \rangle$ or $\vec{\psi} = \langle p \rangle$. Rather, it may be defined as $\vec{\psi} = \langle \psi_1, \psi_2, \psi_3, \ldots, \psi_{n-1}, \psi_n \rangle$ where each of the $\psi$ terms represents an individual exercise intensity input variable that is relevant to the definition of exercise intensity for the case of cycling. These $\psi$ terms may include measurable human performance variables including, but not limited to, power output, cadence, torque, and pace (speed). The $\psi$ terms may include variables relevant to the course where the exercise takes place including, but not limited to, elevation grade. The $\psi$ terms may include environmental factors including, but not limited to, ambient temperature, ambient humidity, and ambient wind velocity. The $\psi$ terms may also include any other variables or factors that are deemed relevant to the definition of exercise intensity for the case of cycling.

For the cases of walking, jogging, and running, the exercise intensity input vector may be expressed as $\vec{\psi} = \langle v, \theta, \omega \rangle$, where v is the pace (speed) of an individual, $\theta$ is the elevation grade, and $\omega$ is their cadence, or frequency of an individual's foot strikes during walking, jogging, or running. It should be noted that $v = L\omega$, where L is the stride length of an individual during walking, jogging, or running. In the event that cadence data is not available for whatever reason, the exercise intensity input vector may be expressed as $\vec{\psi} = \langle v, \theta \rangle$. However, this definition of exercise intensity may reduce the accuracy of model predictions. This loss of accuracy is somewhat mitigated if the individual is exercising at a self-selected cadence though. In the event that elevation grade data is not available for whatever reason, the exercise intensity input vector may be expressed as $\vec{\psi} = \langle v, \omega \rangle$. However, this definition of exercise intensity may reduce the accuracy of model predictions. This loss of accuracy is somewhat mitigated if the individual is exercising at a relatively constant elevation grade though. In the event that cadence and elevation grade data are both not available for whatever reason, the exercise intensity input vector may be expressed as $\vec{\psi} = \langle v \rangle$. However, this definition of exercise intensity may reduce the accuracy of model predictions. This loss of accuracy is somewhat mitigated if the individual is exercising at a relatively constant elevation grade at a self-selected cadence though.

The exercise intensity input vector for walking, jogging, and running is not limited to be defined as $\vec{\psi} = \langle v, \theta, \omega \rangle$, $\vec{\psi} = \langle v, \theta \rangle$, $\vec{\psi} = \langle v, \omega \rangle$, or $\vec{\psi} = \langle v \rangle$. Rather, it may be defined as $\vec{\psi} = \langle \psi_1, \psi_2, \psi_3, \ldots, \psi_{n-1}, \psi_n \rangle$ where each of the $\psi$ terms represents an individual exercise intensity input variable that is relevant to the definition of exercise intensity for the cases of walking, jogging, and running. These $\psi$ terms may include measurable human performance variables including, but not limited to, pace, cadence, and stride length. The $\psi$ terms may include variables relevant to the course where the exercise takes place including, but not limited to, elevation grade. The θ terms may include environmental factors including, but not limited to, ambient temperature, ambient humidity, and ambient wind velocity. The θ terms may also include any other variables or factors that are deemed relevant to the definition of exercise intensity for the cases of walking, jogging, and running.

For the case of swimming, the exercise intensity input vector may be expressed as $\vec{\psi} = \langle v, \omega \rangle$, where v is the pace (speed) of an individual and $\omega$ is their cadence, or frequency of an individual's strokes during swimming. It should be noted that $v = L\omega$, where L is the stroke length of an individual during swimming. In the event that cadence data is not available for whatever reason, the exercise intensity input vector may be expressed as $\vec{\psi} = \langle v \rangle$. However, this definition of exercise intensity may reduce the accuracy of model predictions. This loss of accuracy is somewhat mitigated if the individual is exercising at a self-selected cadence though.

The exercise intensity input vector for swimming is not limited to be defined as $\vec{\psi} = \langle v, \omega \rangle$ or $\vec{\psi} = \langle v \rangle$. Rather, it may be defined as $\vec{\psi} = \langle \psi_1, \psi_2, \psi_3, \ldots, \psi_{n-1}, \psi_n \rangle$ where each of the $\psi$ terms represents an individual exercise intensity input variable that is relevant to the definition of exercise intensity for the case of swimming. These $\psi$ terms may include measurable human performance variables including, but not limited to, pace, cadence, and stroke length. The $\psi$ terms may include variables relevant to the course where the exercise takes place including, but not limited to, elevation grade. The $\psi$ terms may include environmental factors including, but not limited to, ambient water temperature, ambient air temperature, ambient water velocity, ambient wind velocity, and ambient humidity. The ψ terms may also include any other variables or factors that are deemed relevant to the definition of exercise intensity for the case of swimming.

As stated previously, the exercise intensity function $f(\vec{\psi})$ may take many forms, and it is often based on a priori knowledge concerning the active mode of exercise. Alternatively, a generic form for the exercise intensity function $f(\vec{\psi})$ may be used. Without knowing anything about the nature of the exercise intensity function $f(\vec{\psi})$, it is possible to obtain an approximation using a truncated Taylor series expansion, $$f(\vec{\psi}) \approx c_0 + (c_1\psi_1 + c_2\psi_2 + c_3\psi_3 + \ldots + c_{n-1}\psi_{n-1} + c_n\psi_n) + \\ (c_{1,1}\psi_1^2 + c_{2,2}\psi_2^2 + c_{3,3}\psi_3^2 + \ldots + c_{n-1,n-1}\psi_{n-1}^2 + c_{n,n}\psi_n^2) + (c_{1,2}\psi_1\psi_2 + c_{1,3}\psi_1\psi_3 + \ldots + c_{1,n-1}\psi_1\psi_{n-1} + \\ c_{1,n}\psi_1\psi_n + c_{2,3}\psi_2\psi_3 + \ldots + c_{2,n-1}\psi_2\psi_{n-1} + c_{2,n}\psi_2\psi_n + \ldots + c_{n-1,n}\psi_{n-1}\psi_n) + \ldots, \quad (3)$$

where the c terms are constants related to an individual's personal physiology and fitness. The Taylor series expansion may be truncated at any order. However, a second order approximation is recommended to capture nonlinear effects and cross-term relationships. Any approximations less than second order will not capture nonlinear effects or cross-term relationships. Any approximations greater than second order run the risk of over-fitting the model.

For the case of cycling, the exercise intensity function may be represented as $f(\vec{\psi}) = f(p, \omega)$ when considering the exercise intensity input variables of power output p and cadence ω. A Taylor series approximation of this form of the exercise intensity function can be expressed as, $$f(p,\omega) \approx c_0 + c_1 p + c_2 \omega + c_{1,1} p^2 + c_{2,2} \omega^2 + c_{1,2} p\omega + \ldots, \quad (4)$$

where the c terms are constants related to an individual's personal physiology and fitness. In the event that cadence data is not available for whatever reason, the exercise intensity function may be expressed as $f(\vec{\psi}) = f(p)$. However, this definition of the exercise intensity function may reduce the accuracy of model predictions. This loss of accuracy is somewhat mitigated if the individual is exercising at a relatively constant cadence though. A Taylor series approximation of this form of the exercise intensity function can be expressed as, $$f(p) \approx c_0 + c_1 p + c_{1,1} p^2 + \ldots, \quad (5)$$

where the c terms are constants related to an individual's personal physiology and fitness.

These Taylor series expansions may be truncated at any order. However, a second order approximation is recommended to capture nonlinear effects and cross-term relationships. Any approximations less than second order will not capture nonlinear effects or cross-term relationships. Any approximations greater than second order run the risk of over-fitting the model. As stated previously, the exercise intensity function $f(\vec{\psi})$ may take many forms, and these other forms of the exercise intensity function may also be used in this model. These forms of $f(\vec{\psi})$ may be based on a priori knowledge, or they may utilize another generic form. The exercise intensity function for cycling is not limited to be defined as $f(p, \omega)$ or $f(p)$. Rather, it may be defined as $f(\psi_1, \psi_2, \psi_3, \ldots, \psi_{n-1}, \psi_n)$ where each of the ψ terms represents an individual exercise intensity input variable that is relevant to the definition of exercise intensity for the case of cycling. These ψ terms may include measurable human performance variables including, but not limited to, power output, cadence, torque, and pace. The ψ terms may include variables relevant to the course where the exercise takes place including, but not limited to, elevation grade. The ψ terms may include environmental factors including, but not limited to, ambient temperature, ambient humidity, and ambient wind velocity. The ψ terms may also include any other variables or factors that are deemed relevant to the definition of exercise intensity for the case of cycling.

For the cases of walking, jogging, and running, the exercise intensity function may be represented as $f(\vec{\psi}) = f(v, \theta, \omega)$ when considering the exercise intensity input variables of pace v, elevation grade θ, and cadence ω. A Taylor series approximation of this form of the exercise intensity function can be expressed as, $$f(v,\theta,\omega) \approx c_0 + c_1 v + c_2 \theta + c_3 \omega + c_{1,1} v^2 + c_{2,2} \theta^2 + c_{3,3} \omega^2 + c_{1,2} v\theta + c_{1,3} v\omega + c_{2,3} \theta\omega + \ldots, \quad (6)$$

where the c terms are constants related to an individual's personal physiology and fitness. In the event that cadence data is not available for whatever reason, the exercise intensity function may be expressed as $f(\vec{\psi}) = f(v, \theta)$. However, this definition of the exercise intensity function may reduce the accuracy of model predictions. This loss of accuracy is somewhat mitigated if the individual is exercising at a self-selected cadence though. A Taylor series approximation of this form of the exercise intensity function can be expressed as, $$f(v,\theta) \approx c_0 + c_1 v + c_2 \theta + c_{1,1} v^2 + c_{2,2} \theta^2 + c_{1,2} v\theta + \ldots, \quad (7)$$

where the c terms are constants related to an individual's personal physiology and fitness. In the event that elevation grade data is not available for whatever reason, the exercise intensity function may be expressed as $f(\vec{\psi}) = f(v, \omega)$. However, this definition of exercise intensity may reduce the accuracy of model predictions. This loss of accuracy is somewhat mitigated if the individual is exercising at a relatively constant elevation grade though. A Taylor series approximation of this form of the exercise intensity function can be expressed as, $$f(v,\omega) \approx c_0 + c_1 v + c_2 \omega + c_{1,1} v^2 + c_{2,2} \omega^2 + c_{1,2} v\omega + \ldots, \quad (8)$$

where the c terms are constants related to an individual's personal physiology and fitness. In the event that cadence and elevation grade data are both not available for whatever reason, the exercise intensity function may be expressed as $f(\vec{\psi}) = f(v)$. However, this definition of exercise intensity may reduce the accuracy of model predictions. This loss of accuracy is somewhat mitigated if the individual is exercising at a relatively constant elevation grade at a self-selected cadence though. A Taylor series approximation of this form of the exercise intensity function can be expressed as, $$f(v) \approx c_0 + c_1 v + c_{1,1} v^2 + \ldots, \quad (9)$$

where the c terms are constants related to an individual's personal physiology and fitness.

These Taylor series expansions may be truncated at any order. However, a second order approximation is recommended to capture nonlinear effects and cross-term relationships. Any approximations less than second order will not capture nonlinear effects or cross-term relationships. Any approximations greater than second order run the risk of over-fitting the model. As stated previously, the exercise intensity function $f(\vec{\psi})$ may take many forms, and these other forms of the exercise intensity function may also be used in this model. These forms of $f(\vec{\psi})$ may be based on a priori knowledge, or they may utilize another generic form. The exercise intensity function for walking, jogging, and running is not limited to be defined as $f(v, \theta, \omega)$, $f(v, \theta)$, $f(v, \omega)$, or $f(v)$. Rather, it may be defined as $f(\psi_1, \psi_2, \psi_3, \ldots, \psi_{n-1}, \psi_n)$ where each of the $\psi$ terms represents an individual exercise intensity input variable that is relevant to the definition of exercise intensity for the cases of walking, jogging, and running. These $\psi$ terms may include measurable human performance variables including, but not limited to, pace, cadence, and stride length. The $\psi$ terms may include variables relevant to the course where the exercise takes place including, but not limited to, elevation grade. The $\psi$ terms may include environmental factors including, but not limited to, ambient temperature, ambient humidity, and ambient wind velocity. The $\psi$ terms may also include any other variables or factors that are deemed relevant to the definition of exercise intensity for the cases of walking, jogging, and running.

The exercise intensity function $f(\vec{\psi})$ for the case of walking has the same functional form as for the cases of jogging and/or running. However, in operation, these three cases are handled separately for making predictions due to differences in mechanical efficiency among the three modes of exercise. Therefore, for the cases of walking, jogging, and running, the exercise intensity function $f(\vec{\psi})$ may be defined as, $$f(\vec{\psi}) = \begin{cases} f_1(\vec{\psi}) \text{ during walking} \\ f_2(\vec{\psi}) \text{ during jogging} \\ f_3(\vec{\psi}) \text{ during running} \end{cases} \quad (10)$$

with a different exercise intensity function being activated during the individual modes of exercise. Alternatively, if a method for determining the active mode of exercise is not available, then a single exercise intensity function $f(\vec{\psi})$ may be used to represent all three modes of exercise. However, this definition of the exercise intensity function may reduce the accuracy of model predictions. The intermediate jogging phase in particular may be difficult to identify. In such situations, the exercise intensity function $f(\vec{\psi})$ may be defined as, $$f(\vec{\psi}) = \begin{cases} f_1(\vec{\psi}) \text{ during walking} \\ f_2(\vec{\psi}) \text{ during running} \end{cases} \quad (11)$$

with a different exercise intensity function being activated during the individual modes of exercise. Since jogging is an intermediate hybrid exercise mode that can be difficult to correctly identify, this simplified version of the exercise intensity function $f(\vec{\psi})$ that only considers walking and running is sometimes preferable to the three-part model that considers walking, jogging, and running.

For the case of swimming, the exercise intensity function may be represented as $f(\vec{\psi}) = f(v, \omega)$ when considering the exercise intensity input variables of pace $v$ and cadence $\omega$. A Taylor series approximation of this form of the exercise intensity function can be expressed as, $$f(v,\omega) \approx c_0 + c_1 v + c_2 \omega + c_{1,1} v^2 + c_{2,2} \omega^2 + c_{1,2} v\omega + \ldots, \quad (12)$$

where the c terms are constants related to an individual's personal physiology and fitness. In the event that cadence data is not available for whatever reason, the exercise intensity function may be expressed as $f(\vec{\psi})$, $f(v)$. However, this definition of the exercise intensity function may reduce the accuracy of model predictions. This loss of accuracy is somewhat mitigated if the individual is exercising at a self-selected cadence though. A Taylor series approximation of this form of the exercise intensity function can be expressed as, $$f(v) \approx c_0 + c_1 v c_{1,1} v^2 + \ldots, \quad (13)$$

where the c terms are constants related to an individual's personal physiology and fitness.

These Taylor series expansions may be truncated at any order. However, a second order approximation is recommended to capture nonlinear effects and cross-term relationships. Any approximations less than second order will not capture nonlinear effects or cross-term relationships. Any approximations greater than second order run the risk of over-fitting the model. As stated previously, the exercise intensity function $f(\vec{\psi})$ may take many forms, and these other forms of the exercise intensity function may also be used in this model. These forms of $f(\vec{\psi})$ may be based on a priori knowledge, or they may utilize another generic form. The exercise intensity function for swimming is not limited to be defined as $f(v, \omega)$ or $f(v)$. Rather, it may be defined as $f(\psi_1, \psi_2, \psi_3, \ldots, \psi_{n-1}, \psi_n)$ where each of the $\psi$ terms represents an individual exercise intensity input variable that is relevant to the definition of exercise intensity for the case of swimming. These $\psi$ terms may include measurable human performance variables including, but not limited to, pace, cadence, and stroke length. The $\psi$ terms may include variables relevant to the course where the exercise takes place including, but not limited to, elevation grade. The $\psi$ terms may include environmental factors including, but not limited to, ambient water temperature, ambient air temperature, ambient water velocity, ambient wind velocity, and ambient humidity. The $\psi$ terms may also include any other variables or factors that are deemed relevant to the definition of exercise intensity for the case of swimming.

The exercise intensity function $f(\vec{\psi})$ for the case of swimming has the same functional form when applied to various swimming strokes. However, in operation, the individual swimming strokes are handled separately for making predictions due to differences in mechanical efficiency among the swimming strokes. Therefore, for the case of swimming, the exercise intensity function $f(\vec{\psi})$ may be defined as, $$f(\vec{\psi}) = \begin{cases} f_1(\vec{\psi}) \text{ for the front crawl stroke} \\ f_2(\vec{\psi}) \text{ for the backstroke} \\ \vdots \\ f_{m-1}(\vec{\psi}) \text{ for the breaststroke} \\ f_m(\vec{\psi}) \text{ for the butterfly stroke} \end{cases} \quad (14)$$

where m different individual swimming strokes are considered and a different exercise intensity function is activated during the individual swimming strokes. Alternatively, if a method for determining the active swimming stroke is not available, then a single exercise intensity function $f(\vec{\psi})$ may be used to represent all of the swimming strokes. However, this definition of the exercise intensity function may reduce the accuracy of model predictions.

The presented model for heart rate and oxygen uptake dynamics has eight unknown parameters from the core model (Eq 1-2) and an arbitrary number of unknown parameters from the exercise intensity function (Eq 3). Fortunately, a stability analysis of the system's equilibria ($\tilde{u}$, $\tilde{D}$) can be used to restrict the parameter ranges in the system and reduce the number of unknown parameters. The system has three possible equilibria: $\tilde{u}=u_0$, $\tilde{u}=u_x$, and $\tilde{u}=\tilde{D}$. It should be noted that $\tilde{D}=f(\tilde{\bar{\psi}})$, where $f(\tilde{\bar{\psi}})$ is the exercise intensity function evaluated at a constant intensity $\tilde{\bar{\psi}}$. The stability of these equilibria can be determined by evaluating the eigenvalues of the Jacobian matrix for the system. The Jacobian matrix takes the form, $$J = \begin{bmatrix} J_{11} & J_{12} \\ J_{21} & J_{22} \end{bmatrix}, \quad (15)$$

where the elements of the Jacobian are, $$J_{11} = A(\tilde{u}-u_0)^\alpha (u_x-\tilde{u})^\beta (\tilde{D}-\tilde{u})^\gamma \left[\left(\frac{\alpha}{\tilde{u}-u_0}\right) - \left(\frac{\beta}{u_x-\tilde{u}}\right) - \left(\frac{\gamma}{\tilde{D}-\tilde{u}}\right)\right], \quad (16)$$

$$J_{12} = A\gamma(\tilde{u}-u_0)^\alpha (u_x-\tilde{u})^\beta (\tilde{D}-\tilde{u})^{\gamma-1}, \quad (17)$$

$$J_{21} = 0, \quad (18)$$

$$J_{22} = -B\kappa\left(f(\tilde{\bar{\psi}})-\tilde{D}\right)^{\kappa-1}. \quad (19)$$

The eigenvalues $\lambda_{1,2}$ can be found by setting the determinant $|J-\lambda I|=0$. Since $J_{21}=0$, the eigenvalues can be expressed as $$\lambda_1 = J_{11}, \lambda_2 = J_{22}. \quad (20)$$

These eigenvalues determine the stability of the system's equilibria. Since $\tilde{u}=\tilde{D}$ is always stable for $u_0 \leq \tilde{D} \leq u_x$, then $\lambda_{1,2}<0$ at this equilibrium. Therefore, $\gamma=\kappa=1$ and A, B>0. The equilibria at $\tilde{u}=u_0$ and $\tilde{u}=u_x$ are non-hyperbolic fixed points (they exist at the system boundaries), so $\lambda_{1,2}=0$ for these equilibria. Therefore, $\alpha, \beta \neq 1$. One final simplification can be made using the knowledge that $D \geq u_0$, which means that $c_0=u_0$. The number of unknown parameters in the core model can thus be reduced from eight to six, and two of the remaining parameters (A, B) are known to always be positive. The number of unknown parameter in the exercise intensity function was also reduced by one. These parameter reductions and restrictions are significant because they speed up the parameter estimation process when the model is applied to experimental heart rate and oxygen uptake data.

Parameter Estimation Algorithm A parameter estimation algorithm can predict the maximum heart rate or maximal oxygen uptake (or both) of an individual using data collected at submaximal exercise intensities. During the parameter estimation process, all of the other unknown constants from the model and the initial value of the demand function are also determined.

A parameter estimation algorithm is an iterative algorithm that seeks to determine the values of the unknown model parameters through an iterative process. Data for the system inputs $\bar{\psi}$ and the system outputs u are provided to the parameter estimation algorithm, which then proceeds to determine an estimation of the unknown model parameters through an iterative process. Due to the nonlinear nature of the heart rate and oxygen uptake model, a heuristic algorithm is recommended to perform the parameter estimation. Heuristic algorithms encompass a class of algorithms including, but not limited to, genetic algorithms, particle swarm algorithms, and simulated annealing algorithms. The heuristic algorithms can be run multiple times during the parameter estimation process to generate a prediction with uncertainty bounds. Other classes of algorithms may also be utilized to perform the parameter estimation.

Figure 3A:
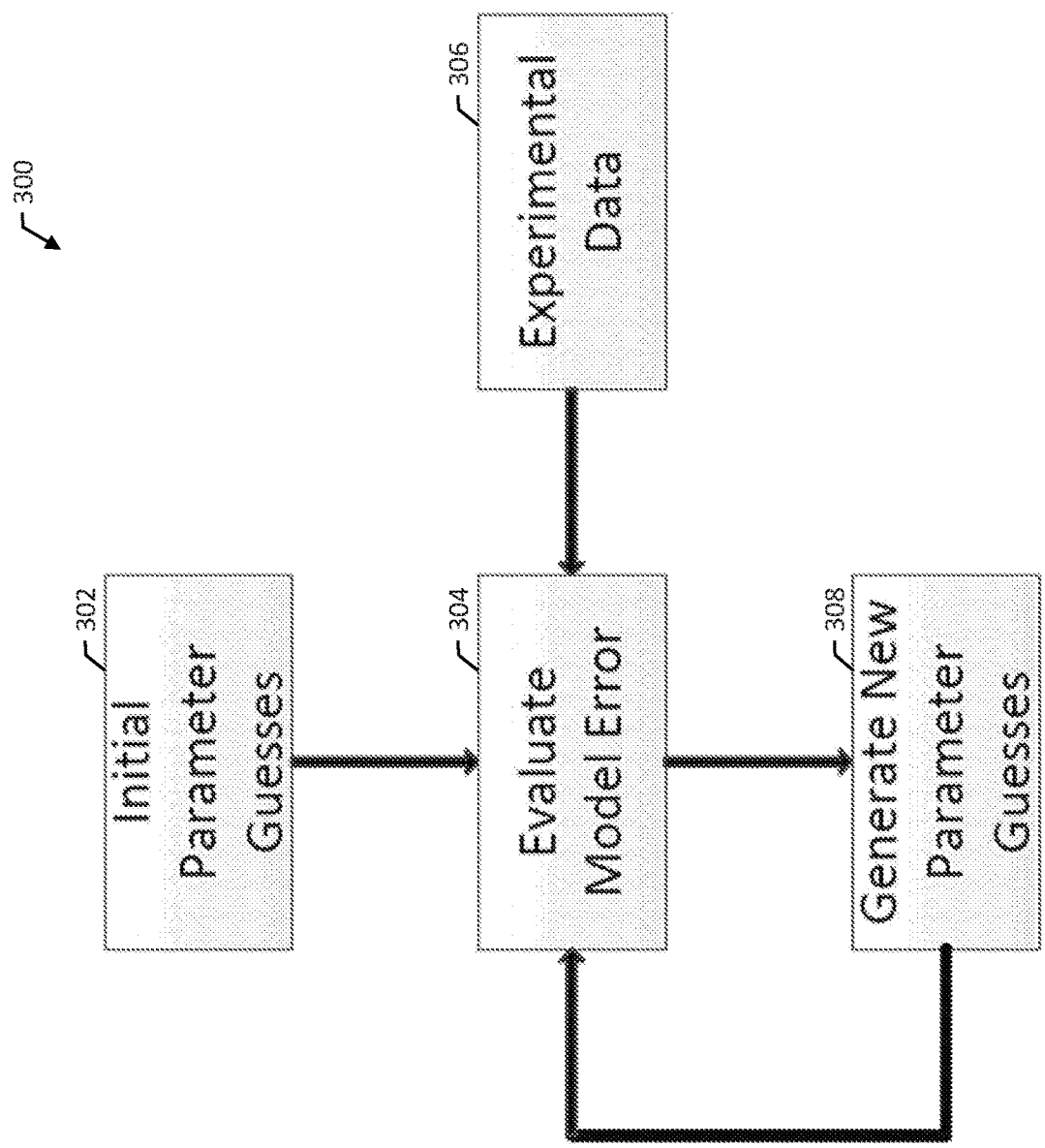
FIGS. 3A-D are flow diagrams illustrating examples of parameter estimation.

FIGS. 3A-D are flow diagrams illustrating examples of parameter estimation. FIG. 3A is a flow diagram of an example parameter estimation method 300. Method 300 includes making initial parameter guesses (302) and evaluating the model error using those initial parameter guesses (304) using experimental data (306). Method 300 includes generating new parameter guesses (308) using the results of evaluating the model error and then re-evaluating the model error using the new parameter guesses (304). Method 300 repeats generating new parameter guesses and evaluating the model error until an end condition is reached, e.g., a target error level or number of iterations is reached.

Figure 3B:
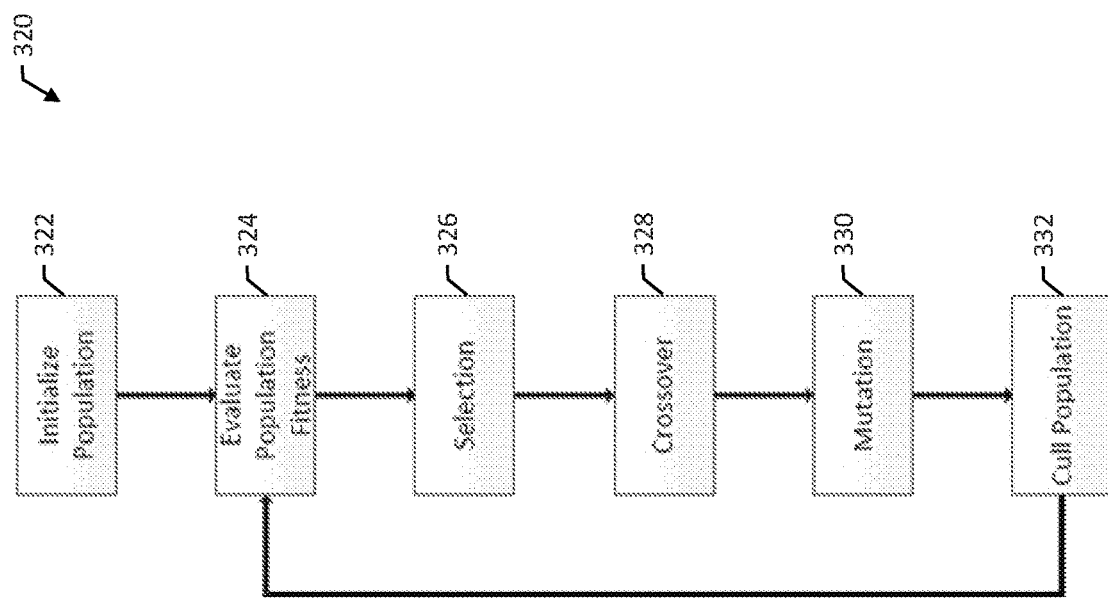

FIG. 3B is a flow diagram of an example genetic algorithm 320. A genetic algorithm is a heuristic evolutionary algorithm that is based on the biological theory of evolution through natural selection. Genetic algorithms iterate a population of solutions over time and utilize evolutionary operators such as, selection, crossover, and mutation to arrive at an optimal solution. Algorithm 320 includes initializing a population (322) and evaluating the population fitness (324). For parameter estimation, the population includes the parameters of the model. Based on the evaluation, algorithm 320 includes selection (326), crossover (328), and mutation (330) to alter the population. Algorithm 320 includes culling the population (332) and repeating the evaluation (324) and then iterating the processes outlined above until an end condition is reached.

Figure 3C:
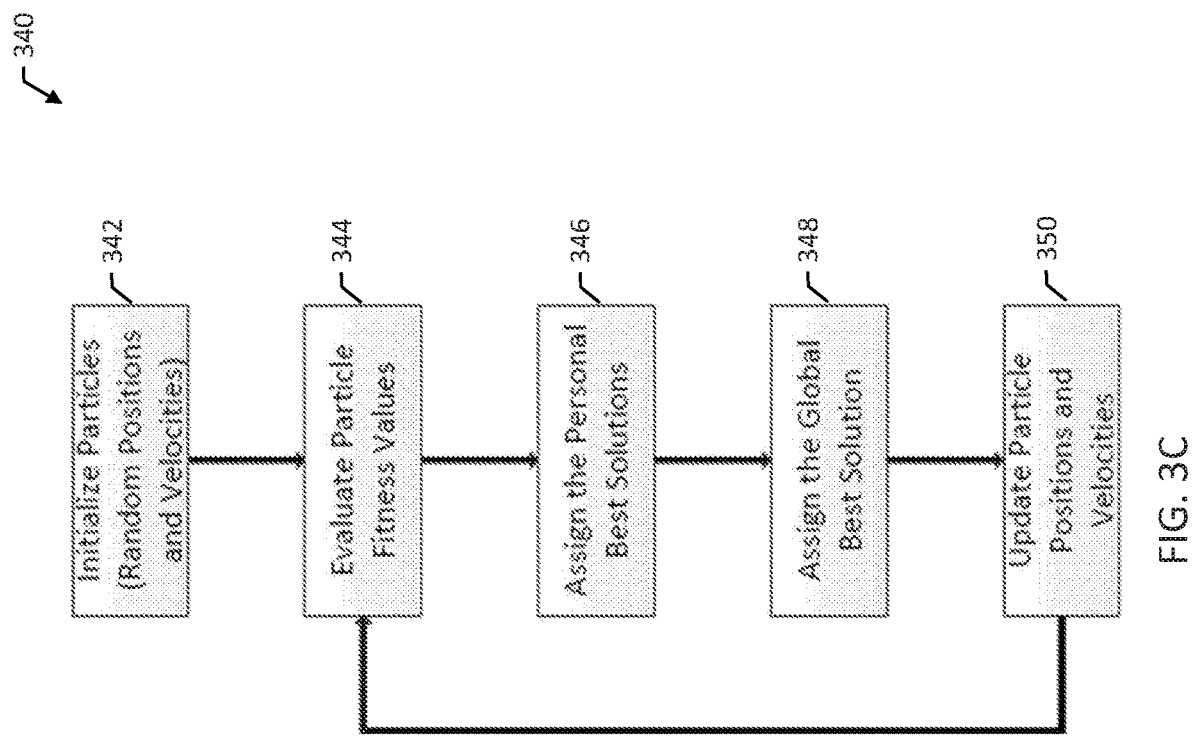

FIG. 3C is a flow diagram of an example particle swarm algorithm 340. A particle swarm algorithm is a heuristic swarm intelligence algorithm that is based on the movement patterns of organisms that travel in groups, such as bird flocks or fish schools. Particle swarm algorithms iterate a population of candidate solutions that search the parameter space with movements that are influenced by both their individual knowledge and the collective knowledge of the swarm to arrive at an optimal solution. Algorithm 340 includes initializing particles with random positions and velocities (342) and evaluating the particle fitness values (344). For parameter estimation, the particle positions represent the parameters of the model. Algorithm 340 includes assigning the personal best solutions (346) and assigning the global best solution (348). Algorithm 340 includes updating the particle positions and velocities (350) and iterating the processes outlined above until an end condition is reached.

Figure 3D:
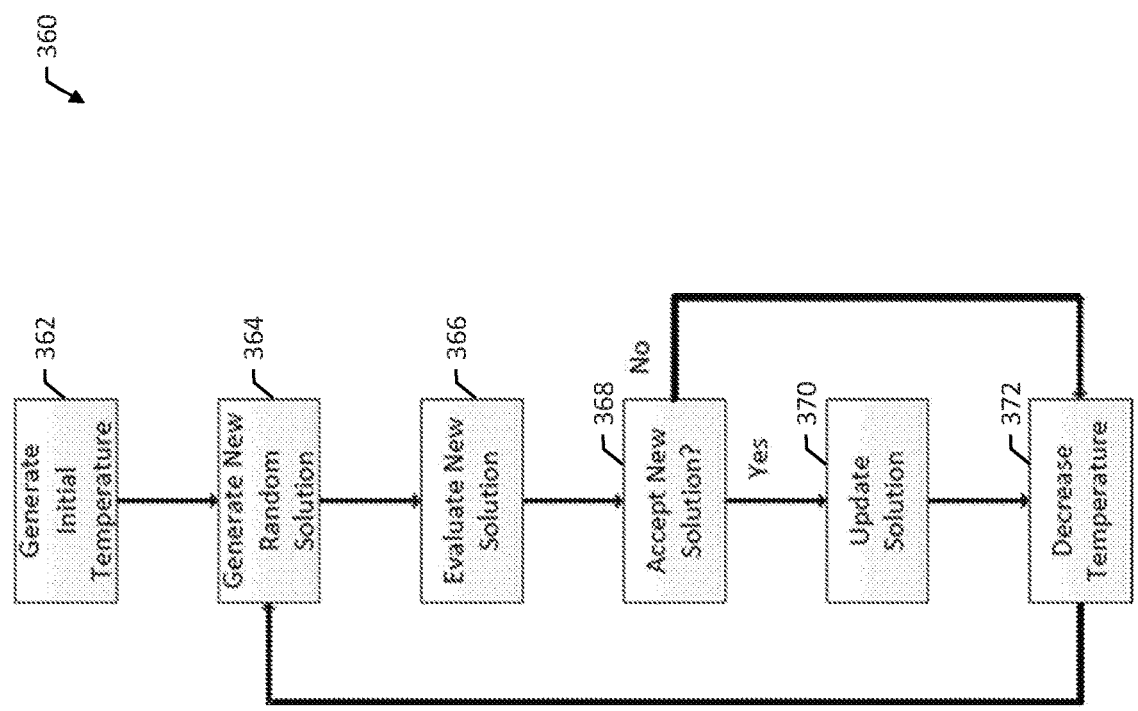

FIG. 3D is a flow diagram of an example simulated annealing algorithm 360. A simulated annealing algorithm is a heuristic stochastic algorithm that is based on the metallurgical process of annealing. During the simulated annealing process, the parameter space is explored freely when the artificial "temperature" is high. However, as artificial "cooling" occurs, this exploration is slowly restricted such that the probability of accepting worse solutions decreases. Algorithm 360 includes generating an initial temperature (362) and generating a new random solution at the initial temperature (364). Algorithm 360 includes evaluating the new solution (366) and determining whether to accept the new solution (368). If so, then algorithm 360 includes updating the solution (370). Algorithm 360 includes decreasing the temperature (372) and iterating the processes outlined above until an end condition is reached.

System Implementation

Human subject tests have validated the method for predicting maximum heart rate and maximal oxygen uptake from submaximal exercise intensities. The participants in the human subject tests each performed a maximal cardiopulmonary exercise test (CPET) in the laboratory to determine their maximum heart rate and maximal oxygen uptake. Some subjects performed the test on an electronically-braked cycle ergometer, and other subjects performed the test on a treadmill. The subjects then returned to the laboratory within a week of the initial test to perform a submaximal cardiopulmonary exercise test on the same equipment that they were initially tested on.

A computer system then applied the model and parameter estimation algorithm to their submaximal exercise data to make predictions for their maximum heart rate and maximal oxygen uptake. It was possible to use small subsets of the data (e.g., 10 min) to make accurate predictions. The submaximal model predictions were compared to the true experimental values obtained during the maximal cardiopulmonary exercise test and reported a coefficient of determination ($R^2$) of 0.96 and a standard error of the estimate (SEE) of 2.4 bpm for maximum heart rate and a coefficient of determination of 0.93 and a standard error of the estimate of 2.1 mL $kg^{-1} \cdot min^{-1}$ for maximal oxygen uptake. For comparison, traditional submaximal estimation methods report a standard error of the estimate of at least 10 bpm for maximum heart rate and a standard error of the estimate of at least 4 mL·$kg^{-1} \cdot min^{-1}$ for maximal oxygen uptake. A secondary objective of these human subject tests was to demonstrate how the model can replicate the time series responses for the heart rate and oxygen uptake signals. The coefficient of determination for the heart rate time series predictions was 0.89±0.04. The coefficient of determination for the oxygen uptake time series predictions was 0.91±0.02.

Figure 4:
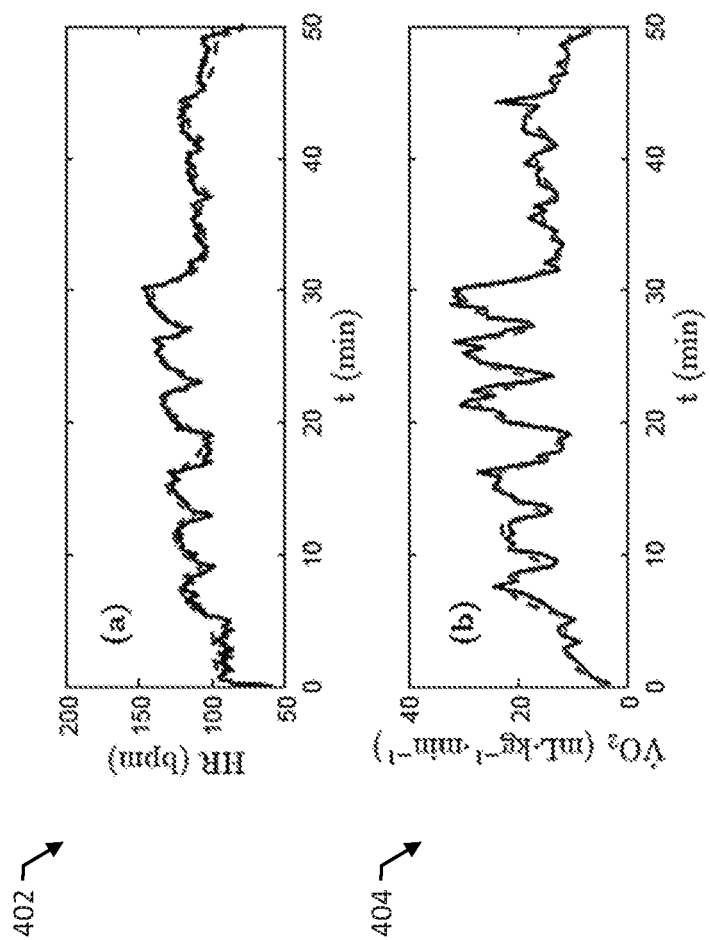
FIG. 4 shows an example of the time series model predictions.

FIG. 4 shows an example of the time series model predictions. FIG. 4 shows: (a) a chart 402 illustrating model predictions as dashed lines against measured values as solid lines for heart rate and; (b) a chart 404 illustrating model predictions as dashed lines against measured values as solid lines for oxygen uptake.

Figure 5:
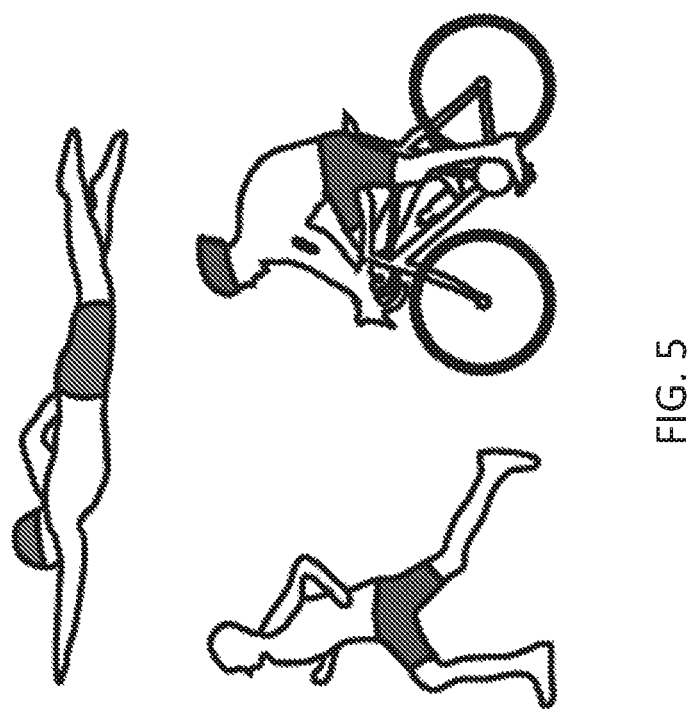
FIG. 5 illustrates that the system can be used by individuals participating in a variety of exercise activities.

FIG. 5 illustrates that the system can be used by individuals participating in a variety of exercise activities (e.g., running, cycling, and swimming). In the equations given above, the exercise intensity is defined relative to walking, jogging, running, cycling, and swimming. However, it is also possible to define exercise intensity for other physical activities including, but not limited to, hand-cycling, hiking, skating, and jumping. Exercise intensity can be measured using stationary equipment (e.g., a cycle ergometer or treadmill) or from a wearable electronic fitness monitor (e.g., a GPS watch).

Figure 6:
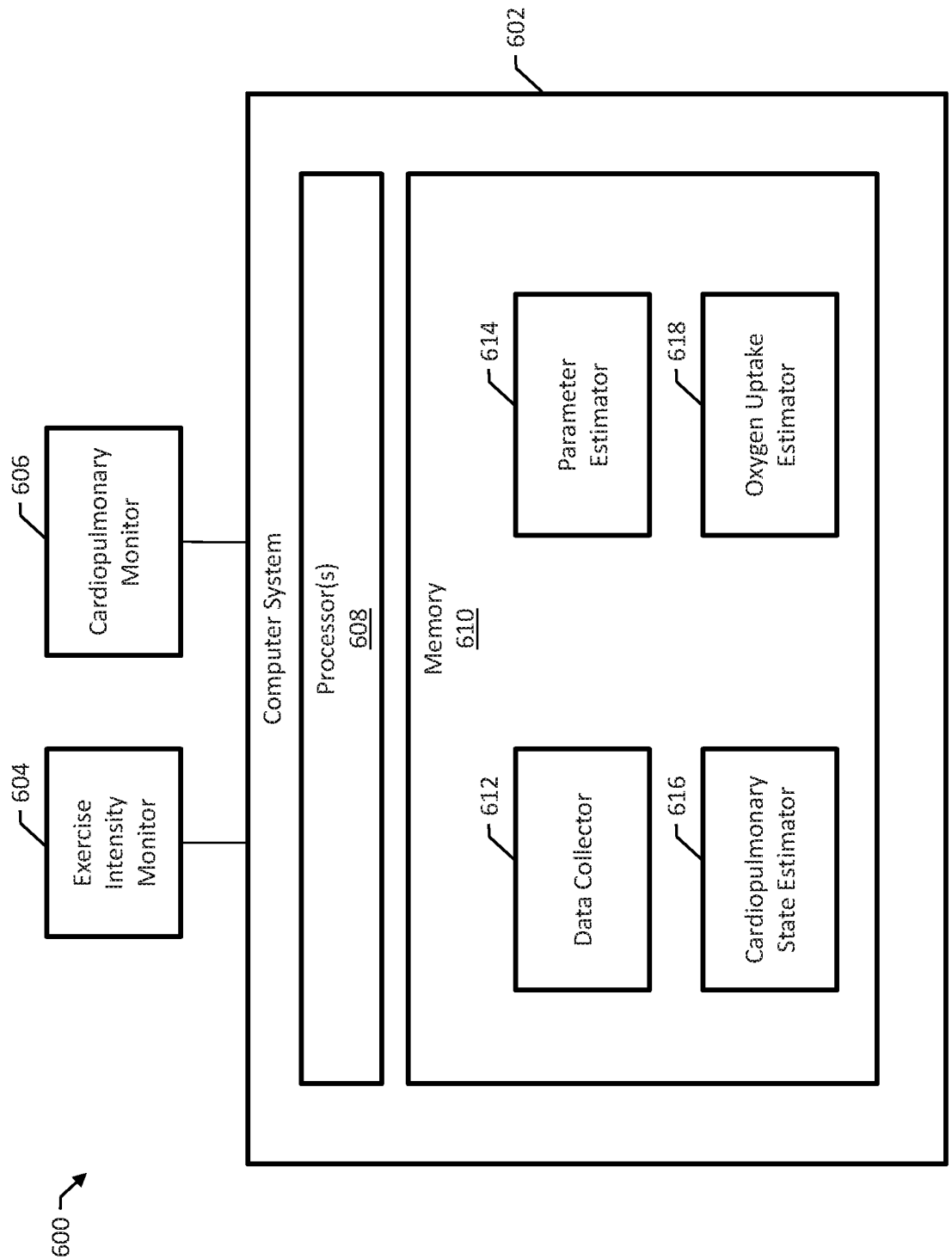
FIG. 6 is a block diagram of an example system for estimating maximum heart rate and maximal oxygen uptake from submaximal exercise intensities.

FIG. 6 is a block diagram of an example system 600 for estimating maximum heart rate and maximal oxygen uptake from submaximal exercise intensities. The system 600 includes a computer system 602, an exercise intensity monitor 604, and a cardiopulmonary monitor 606. The computer system 602 includes one or more processors 608 and memory 610 storing instructions that, when executed by the processors 608, cause the processors 608 to implement a maximal cardiopulmonary estimator by performing operations, e.g., as described above with respect to FIGS. 1-5. In some examples, the system 600 includes or is operatively associated with a wearable fitness device.

The exercise intensity monitor 604 can be implemented as any appropriate type of monitor for an exercise test. For example, the exercise intensity monitor 604 can be power meter pedals installed on a cycle ergometer for measuring instantaneous power output and cadence data during a cycling test. In another example, the exercise intensity monitor 604 can be a measurement device in a treadmill for measuring pace, elevation grade, and/or cadence during a walking, jogging, or running test.

In some examples, the cardiopulmonary monitor 606 is a heart rate monitor, e.g., an electronic device using a pair of electrodes or an optical sensor for providing heart rate readings. In some examples, the cardiopulmonary monitor 606 is an oxygen uptake monitor, e.g., a metabolic system including a mask with a breathing tube connected to oxygen and carbon dioxide analyzers to measure consumption and output. The system 600 can include more than one type of cardiopulmonary monitor (e.g., both a hear rate monitor and an oxygen uptake monitor) and/or other types of fitness monitors. For example, the system 600 can include a blood pressure monitor, a pulse oximeter, and/or an inertial measurement unit (IMU).

The computer system 602 includes a data collector 612 for receiving submaximal exercise intensity data from the exercise intensity monitor 604 and submaximal cardiopulmonary data from the cardiopulmonary monitor 606 while a user, who coupled to the exercise intensity monitor and the cardiopulmonary monitor, is performing an exercise at a submaximal exercise intensity. The computer system 602 also includes a parameter estimator 614 for executing a parameter estimation algorithm to estimate parameters for a nonlinear model of cardiopulmonary dynamics for the user. The computer system 602 also includes a cardiopulmonary state estimator 616 for determining an estimate of a maximal cardiopulmonary state of the user based on the submaximal exercise intensity data and the submaximal cardiopulmonary data. In some examples, the cardiopulmonary state estimator 616 is configured for estimating, using the nonlinear model of cardiopulmonary dynamics for the user, a resting cardiopulmonary state of the user based on the submaximal exercise intensity data and the submaximal cardiopulmonary data.

Receiving submaximal cardiopulmonary data can include receiving a time series of oxygen uptake readings, and then determining the estimate of the maximal cardiopulmonary state of the user includes estimating a maximal oxygen uptake for the user. Similarly, receiving submaximal cardiopulmonary data can include receiving a time series of heart rate readings, and then determining the estimate of the maximal cardiopulmonary state of the user includes estimating a maximum heart rate for the user.

Receiving submaximal exercise intensity data from the exercise intensity monitor and submaximal cardiopulmonary data from the cardiopulmonary monitor can include time synchronizing the submaximal exercise intensity data and the submaximal cardiopulmonary data. For example, suppose that the submaximal exercise intensity data is sampled once every second and that the submaximal cardiopulmonary data is sampled once every ten seconds. Synchronizing the data can include matching the data to a common sampling frequency.

In some examples, the nonlinear model of cardiopulmonary dynamics includes an exercise intensity function $f(\vec{\psi})$ which drives the rate of change of cardiopulmonary demand by the user while performing the exercise. The parameters can be coefficients of a truncated Taylor series expansion approximating the exercise intensity function $f(\vec{\psi})$. Then, executing the parameter estimation algorithm includes executing an algorithm to fit the parameters to the submaximal exercise intensity data and the submaximal cardiopulmonary data in the nonlinear model of cardiopulmonary dynamics. The parameter estimation algorithm may be a heuristic algorithm such as a genetic algorithm, particle swarm algorithm, or simulated annealing algorithm. Other classes of algorithms may also be utilized to perform the parameter estimation.

In some examples, the computer system 602 includes an oxygen uptake estimator 618. The oxygen uptake estimator 618 is configured to estimate oxygen uptake values for a user during an exercise test without the need for an oxygen uptake monitor. The oxygen uptake estimator 618 can estimate oxygen uptake using inputs from the cardiopulmonary monitor 606 (e.g., heart rate monitor), the exercise intensity monitor 604, and/or other sources of fitness data (e.g., pulse oximeter). For example, the inputs to the oxygen uptake estimator 618 can include some combination of variables including, but not limited to, heart rate, the time derivative of heart rate, oxygen saturation, exercise intensity inputs (e.g., power output and cadence for cycling), gender, body mass, height, and/or body mass index (BMI).

The oxygen uptake estimator 618 can be implemented using a regression model generated by any appropriate technique to determine a relationship between the independent variables (system inputs) and the dependent variable (oxygen uptake). A regression model may be defined as any prediction model that takes the following form, $$y \approx f_R(\vec{x}, \vec{\mu}), \qquad (21)$$

where y is the dependent variable, $\vec{x}$ is a vector of independent variables, $\vec{\mu}$ is a vector of unknown regression parameters, and $f_R$ is a regression function. The regression function $f_R$ may take many forms, and it is often based on a priori knowledge concerning the relationship between $\vec{x}$ and y. Alternatively, a generic form for $f_R$ may be chosen.

The regression model can be trained by providing it with observed data points $\langle \vec{x}, y \rangle$, which are then used to solve for $\vec{\mu}$. A regression model may utilize cross-validation methods during the training process to prevent over-fitting of the data. During the cross-validation process, the observed data is partitioned into subsets. Only some of the subsets can be used for training, with the remaining subsets used for validation. This process may be iterated, with different subsets being used for training and validation.

Figure 7:
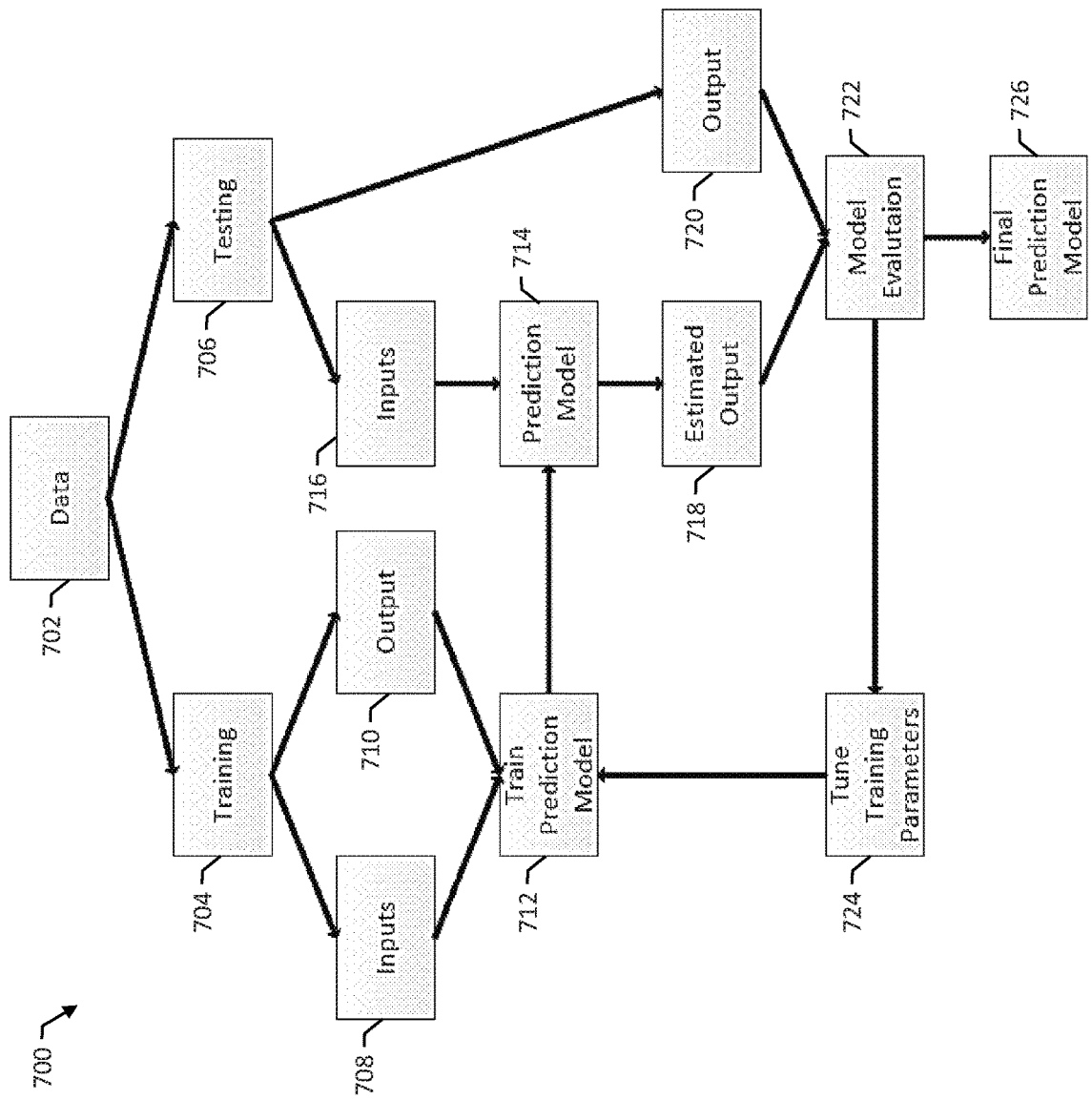
FIG. 7 is a flow diagram of an example technique 700 for training a regression model.

FIG. 7 is a flow diagram of an example technique 700 for training a regression model. Data 702 is divided into training data 704 and testing data 706. The training data 704 is divided into inputs 708 (e.g., heart rate, the time derivative of heart rate, oxygen saturation, exercise intensity inputs) and output 710 (measured oxygen uptake) that are used to train a prediction model (712). The resulting prediction model 714 is then applied to the inputs 716 of the testing data 706 to produce an estimated output 718 for a model evaluation 722 using the output 720 of the testing data 706. The result of the evaluation is then used to tune training parameters (724) for the prediction model, and the processes outlined above are then repeated until an end condition is reached, e.g., a satisfactory error rate or a maximum number of iterations, resulting in a final prediction model (726).

The regression model for estimating oxygen uptake may be implemented using an artificial neural network (ANN). An artificial neural network is a computational machine learning method that is loosely based on the process by which a biological brain solves problems. An artificial neural network comprises three types of neurons or nodes: the inputs nodes which represent the independent variables (system inputs), the hidden nodes which are functions of the input nodes, and the output node, which is a function of the hidden nodes and represents the dependent variable (oxygen uptake).

Figure 8A:
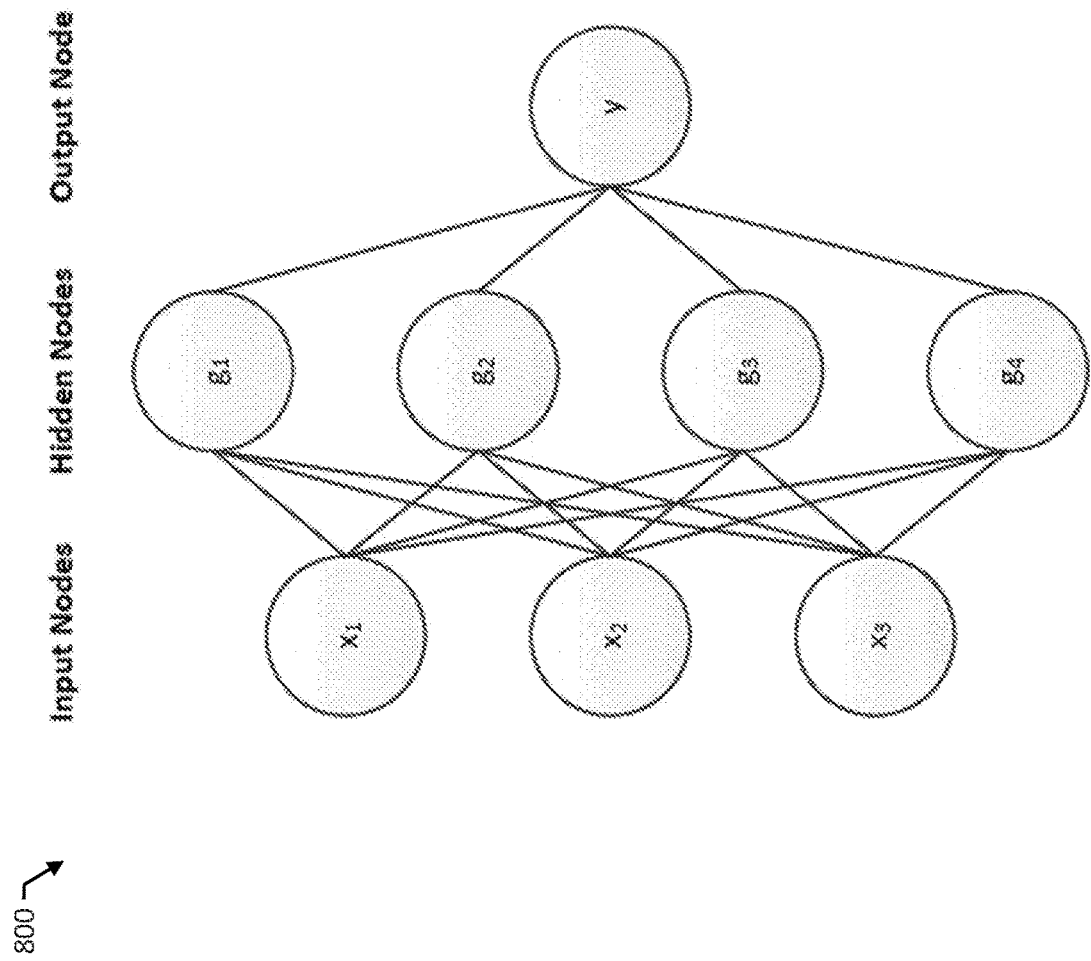
FIGS. 8A-B illustrate example artificial neural networks.
Figure 8B:
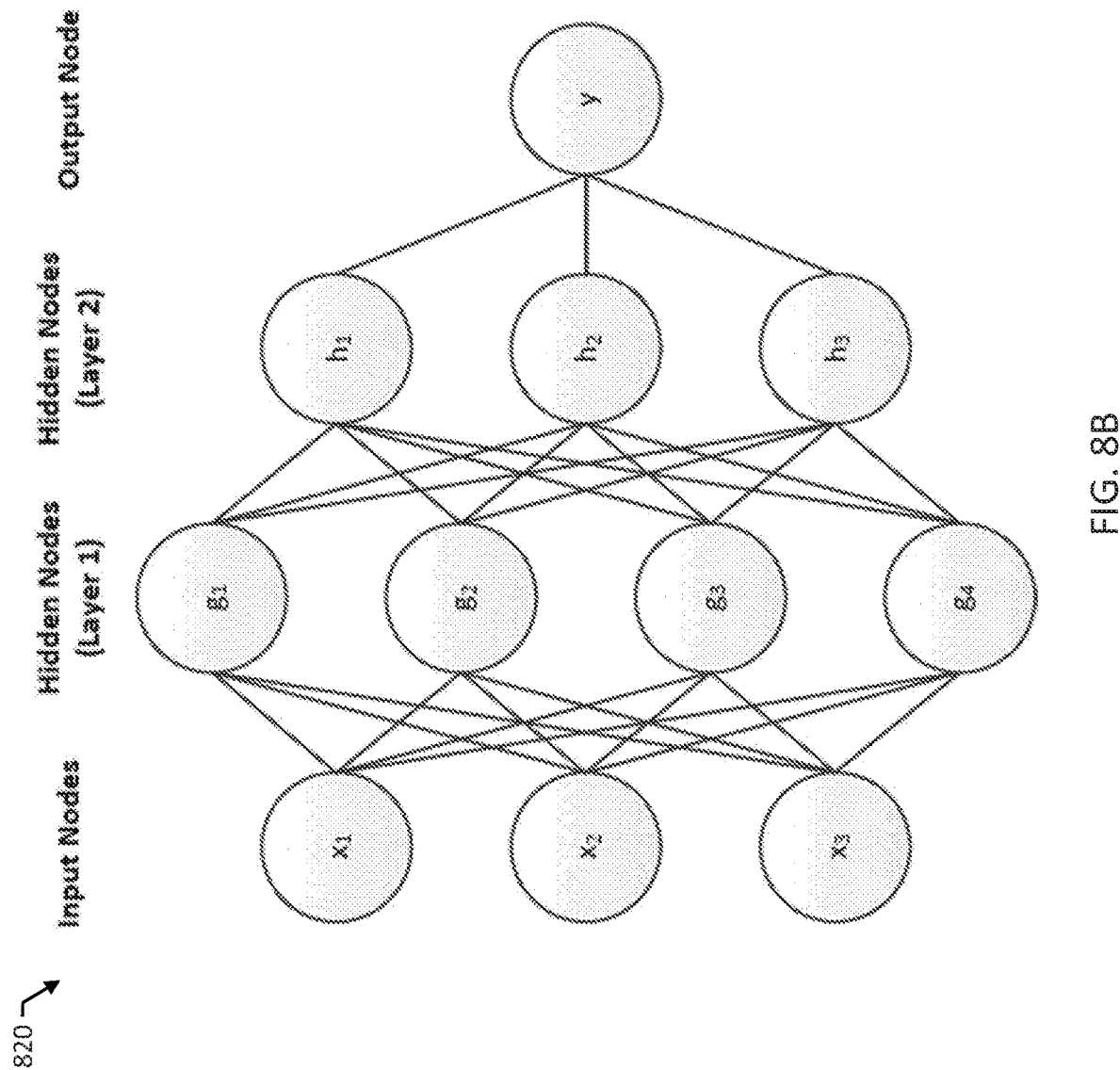

FIGS. 8A-B illustrate example artificial neural networks. FIG. 8A illustrates an example of nodes of an artificial neural network 800, including input nodes $x_1$-$x_3$, hidden nodes $g_1$-$g_4$, and an output node y. An artificial neural network may be defined using the following nonlinear weighted sum, $$y \approx K(\Sigma_i w_i g_i(\vec{x})), \qquad (22)$$

where y is the dependent variable, $\vec{x}$ is a vector of independent variables, $g_i$ is a hidden node with its corresponding weight $w_i$, and K is the so-called activation function. The activation function is often based on a priori knowledge concerning the relationship between $\vec{x}$ and y. Alternatively, a generic form for K may be chosen from the class of so-called activation functions including, but not limited to, the hyperbolic tangent function, the logistic function, and the softmax function.

An artificial neural network may contain any number of hidden nodes arranged into single or multi-layer configurations. FIG. 8B illustrates an example of nodes of a multi-layer artificial neural network 820, including input nodes $x_1$-$x_3$, hidden nodes $g_1$-$g_4$ in a first layer, hidden nodes $h_1$-$h_3$ in a second layer, and an output node y. When generating a regression model, the weights associated with the interconnections between the input nodes, hidden nodes, and output node are tuned using the so-called backpropagation algorithm. During the training process, cross-validation techniques may be employed.

CONCLUSIONS

This specification describes methods and systems for predicting the maximum heart rate and maximal oxygen uptake for an individual using data collected at submaximal exercise intensities. The method is able to make predictions with a level of accuracy far greater than conventional methods, which rely on linear models and population-specific assumptions. The model is able to account for person-specific physiology, including the nonlinear aspects of the heart rate and oxygen uptake responses. The model enables a computer system to predict the maximum heart rate and maximal oxygen uptake for an individual using data collected at submaximal exercise intensities. Specifically, the computer system can use a set of state equations in conjunction with an exercise intensity function.

This specification has described exercise intensity for the cases of walking, jogging, running, cycling, and swimming. However, exercise intensity can be defined for other physical activities including, but not limited to, hand-cycling, hiking, skating, and jumping. Therefore, maximum heart rate and maximal oxygen uptake predictions can be made using a wide range of exercise options. A computer system can execute a parameter estimation algorithm to perform the estimation. Due to the nonlinear nature of the dynamical system model, it is recommended that the parameter estimation algorithm consist of a heuristic algorithm. Heuristic algorithms encompass a class of algorithms including, but not limited to, genetic algorithms, particle swarm algorithms, and simulated annealing algorithms. The heuristic algorithms can be run multiple times during the parameter estimation process to generate a prediction with uncertainty bounds. However, other types of parameter estimation algorithms could potentially be applied to this model as well. The systems and methods described in this specification could be implemented with existing heart rate monitors and fitness tracking technologies, which would enable those systems and methods to be accessible to a large and diverse population of individuals.

It is understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system comprising:
    an exercise intensity monitor;
    a cardiopulmonary monitor; and
    one or more computers configured to perform operations comprising:
        receiving submaximal exercise intensity data from the exercise intensity monitor and submaximal cardiopulmonary data from the cardiopulmonary monitor while a user coupled to the exercise intensity monitor and the cardiopulmonary monitor is performing an exercise at a submaximal exercise intensity;
        determining a heuristic estimate of a maximal cardiopulmonary state of the user based on the submaximal exercise intensity data, the submaximal cardiopulmonary data, and a nonlinear model of cardiopulmonary dynamics for the user, wherein the nonlinear model of cardiopulmonary dynamics includes an exercise intensity function that drives the rate of change of cardiopulmonary demand by the user while performing the exercise; and
        determining a heuristic estimate of a resting cardiopulmonary state of the user based on the submaximal exercise intensity data and the submaximal cardiopulmonary data.

2. The system of claim 1, wherein the cardiopulmonary monitor is a heart rate monitor, wherein receiving submaximal cardiopulmonary data comprises receiving a time series of heart rate readings from the heart rate monitor, and wherein determining the heuristic estimate of the maximal cardiopulmonary state of the user comprises determining a maximum heart rate of the user.

3. The system of claim 1, wherein the cardiopulmonary monitor is an oxygen uptake monitor, wherein receiving submaximal cardiopulmonary data comprises receiving a time series of oxygen uptake readings from the oxygen uptake monitor, and wherein determining the heuristic estimate of the maximal cardiopulmonary state of the user comprises determining a maximal oxygen uptake for the user.

4. The system of claim 1, comprising an exercise bicycle, wherein the exercise intensity monitor comprises a cycling power meter coupled to the exercise bicycle, and wherein receiving submaximal exercise intensity data from the exercise intensity monitor comprises receiving a time series of power output, cadence, and/or torque measurements from the cycling power meter.

5. The system of claim 1, comprising a treadmill, wherein receiving submaximal exercise intensity data from the exercise intensity monitor comprises receiving a time series of pace, elevation grade, and/or cadence measurements from the treadmill.

6. The system of claim 1, wherein receiving submaximal exercise intensity data from the exercise intensity monitor comprises receiving, while the user is cycling, a time series of a combination of one or more of: power output, cadence, torque, pace, elevation grade, ambient temperature, ambient humidity, and/or ambient wind velocity.

7. The system of claim 1, wherein receiving submaximal exercise intensity data from the exercise intensity monitor comprises receiving, while the user is walking or jogging or running, a time series of a combination of one or more of: pace, cadence, stride length, elevation grade, ambient temperature, ambient humidity, and/or ambient wind velocity.

8. The system of claim 1, wherein receiving submaximal exercise intensity data from the exercise intensity monitor comprises receiving, while the user is swimming, a time series of a combination of one or more of: pace, cadence, stroke length, elevation grade, ambient water temperature, ambient air temperature, ambient water velocity, ambient wind velocity, and/or ambient humidity.

9. The system of claim 1, wherein receiving submaximal exercise intensity data from the exercise intensity monitor and submaximal cardiopulmonary data from the cardiopulmonary monitor comprises time synchronizing the submaximal exercise intensity data and the submaximal cardiopulmonary data.

10. The system of claim 1, wherein determining a heuristic estimate of a maximal cardiopulmonary state of the user comprises executing a parameter estimation algorithm to estimate a plurality of parameters for the nonlinear model of cardiopulmonary dynamics for the user and using the plurality of parameters to determine the heuristic estimate of the maximal cardiopulmonary state of the user.

11. The system of claim 10, wherein at least some of the plurality of parameters comprise coefficients of a truncated Taylor series expansion approximating the exercise intensity function.

12. The system of claim 10, wherein executing the parameter estimation algorithm comprises executing a genetic algorithm, a particle swarm algorithm, or a simulated annealing algorithm to fit the plurality of parameters to the submaximal exercise intensity data and the submaximal cardiopulmonary data in the nonlinear model of cardiopulmonary dynamics.

13. The system of claim 1, the operations comprising estimating oxygen uptake data for the user using submaximal cardiopulmonary data, submaximal exercise intensity data, and a regression model trained using training data specifying system input training values and oxygen uptake training values, and wherein determining the heuristic estimate of the maximal cardiopulmonary state of the user comprises determining a maximal oxygen uptake for the user using the estimated oxygen uptake data.

14. The system of claim 13, the operations comprising receiving system input data including a combination of one or more of: heart rate, the time derivative of heart rate, oxygen saturation, exercise intensity inputs, gender, body mass, height, and/or body mass index (BMI), and wherein estimating oxygen uptake data comprises supplying the system input data to the regression model.

15. The system of claim 13, wherein the regression model comprises an artificial neural network (ANN).

16. A wearable device comprising:
one or more processors operatively associated with an exercise intensity monitor and a cardiopulmonary monitor; and
a maximal cardiopulmonary estimator implemented using the one or more processors to perform operations comprising:
receiving submaximal exercise intensity data from the exercise intensity monitor and submaximal cardiopulmonary data from the cardiopulmonary monitor while a user coupled to the exercise intensity monitor and the cardiopulmonary monitor is performing an exercise at a submaximal exercise intensity;
determining a heuristic estimate of a maximal cardiopulmonary state of the user based on the submaximal exercise intensity data, the submaximal cardiopulmonary data, and a nonlinear model of cardiopulmonary dynamics for the user, wherein the nonlinear model of cardiopulmonary dynamics includes an exercise intensity function that drives the rate of change of cardiopulmonary demand by the user while performing the exercise; and
determining a heuristic estimate of a resting cardiopulmonary state of the user based on the submaximal exercise intensity data and the submaximal cardiopulmonary data.

17. The wearable device of claim 16, wherein the cardiopulmonary monitor is a heart rate monitor, wherein receiving submaximal cardiopulmonary data comprises receiving a time series of heart rate readings from the heart rate monitor, and wherein determining the heuristic estimate of the maximal cardiopulmonary state of the user comprises determining a maximum heart rate of the user.

18. The wearable device of claim 16, wherein the cardiopulmonary monitor is an oxygen uptake monitor, wherein receiving submaximal cardiopulmonary data comprises receiving a time series of oxygen uptake readings from the oxygen uptake monitor, and wherein determining the heuristic estimate of the maximal cardiopulmonary state of the user comprises determining a maximal oxygen uptake for the user.

19. The wearable device of claim 16, wherein the exercise intensity monitor comprises a cycling power meter coupled to an exercise bicycle, and wherein receiving submaximal exercise intensity data from the exercise intensity monitor comprises receiving a time series of power output, cadence, and torque measurements from the cycling power meter.

20. The wearable device of claim 16, wherein receiving submaximal exercise intensity data from the exercise intensity monitor comprises receiving a time series of pace, elevation grade, and/or cadence measurements from a treadmill.

21. The wearable device of claim 16, wherein receiving submaximal exercise intensity data from the exercise intensity monitor comprises receiving, while the user is cycling, a time series of a combination of one or more of: power output, cadence, torque, pace, elevation grade, ambient temperature, ambient humidity, and/or ambient wind velocity.

22. The wearable device of claim 16, wherein receiving submaximal exercise intensity data from the exercise intensity monitor comprises receiving, while the user is walking or jogging or running, a time series of a combination of one or more of: pace, cadence, stride length, elevation grade, ambient temperature, ambient humidity, and/or ambient wind velocity.

23. The wearable device of claim 16, wherein receiving submaximal exercise intensity data from the exercise intensity monitor comprises receiving, while the user is swimming, a time series of a combination of one or more of: pace, cadence, stroke length, elevation grade, ambient water temperature, ambient air temperature, ambient water velocity, ambient wind velocity, and/or ambient humidity.

24. The wearable device of claim 16, wherein receiving submaximal exercise intensity data from the exercise intensity monitor and submaximal cardiopulmonary data from the cardiopulmonary monitor comprises time synchronizing the submaximal exercise intensity data and the submaximal cardiopulmonary data.

25. The wearable device of claim 16, wherein determining a heuristic estimate of a maximal cardiopulmonary state of the user comprises executing a parameter estimation algorithm to estimate a plurality of parameters for the nonlinear model of cardiopulmonary dynamics for the user and using the plurality of parameters to determine the heuristic estimate of the maximal cardiopulmonary state of the user.

26. The wearable device of claim 25, wherein at least some of the plurality of parameters comprise coefficients of a truncated Taylor series expansion approximating the exercise intensity function.

27. The wearable device of claim 25, wherein executing the parameter estimation algorithm comprises executing a genetic algorithm, a particle swarm algorithm, or a simulated annealing algorithm to fit the plurality of parameters to the submaximal exercise intensity data and the submaximal cardiopulmonary data in the nonlinear model of cardiopulmonary dynamics.

28. The wearable device of claim 16, the operations comprising estimating oxygen uptake data for the user using submaximal cardiopulmonary data, submaximal exercise intensity data, and a regression model trained using training data specifying system input training values and oxygen uptake training values, and wherein determining the heuristic estimate of the maximal cardiopulmonary state of the user comprises determining a maximal oxygen uptake for the user using the estimated oxygen uptake data.

29. The wearable device of claim 28, the operations comprising receiving system input data including a combination of one or more of: heart rate, the time derivative of heart rate, oxygen saturation, exercise intensity inputs, gender, body mass, height, and/or body mass index (BMI), and wherein estimating oxygen uptake data comprises supplying the system input data to the regression model.

30. The wearable device of claim 28, wherein the regression model comprises an artificial neural network (ANN).

31. A method performed by one or more computers, the method comprising:
receiving submaximal exercise intensity data from an exercise intensity monitor and submaximal cardiopulmonary data from a cardiopulmonary monitor while a user coupled to the exercise intensity monitor and the cardiopulmonary monitor is performing an exercise at a submaximal exercise intensity;
determining a heuristic estimate of a maximal cardiopulmonary state of the user based on the submaximal exercise intensity data, the submaximal cardiopulmonary data, and a nonlinear model of cardiopulmonary dynamics for the user, wherein the nonlinear model of cardiopulmonary dynamics includes an exercise intensity function that drives the rate of change of cardiopulmonary demand by the user while performing the exercise; and determining a heuristic estimate of a resting cardiopulmonary state of the user based on the submaximal exercise intensity data and the submaximal cardiopulmonary data.

* * * * *